United States Patent
Zhang et al.

(10) Patent No.: US 9,695,141 B2
(45) Date of Patent: Jul. 4, 2017

(54) ANTICANCER MILIUSANE DERIVATIVES

(71) Applicant: Hong Kong Baptist University, Hong Kong (HK)

(72) Inventors: Hongjie Zhang, Hong Kong (HK); Yifu Guan, Hong Kong (HK)

(73) Assignee: HONG KONG BAPTIST UNIVERSITY, Kowloon Tong, Kowloon (HK)

( * ) Notice: Subject to any disclaimer, the term of this patent is extended or adjusted under 35 U.S.C. 154(b) by 0 days.

(21) Appl. No.: 14/927,485

(22) Filed: Oct. 30, 2015

(65) Prior Publication Data
US 2016/0046594 A1   Feb. 18, 2016

Related U.S. Application Data

(63) Continuation-in-part of application No. 13/831,997, filed on Mar. 15, 2013, now Pat. No. 9,211,333.

(51) Int. Cl.
| | |
|---|---|
| *C07D 307/94* | (2006.01) |
| *A61K 45/06* | (2006.01) |
| *A61K 31/403* | (2006.01) |
| *A61K 31/365* | (2006.01) |
| *C07D 209/54* | (2006.01) |
| *A61K 31/343* | (2006.01) |
| *A61K 31/4025* | (2006.01) |

(52) U.S. Cl.
CPC .......... *C07D 307/94* (2013.01); *A61K 31/343* (2013.01); *A61K 31/365* (2013.01); *A61K 31/403* (2013.01); *A61K 31/4025* (2013.01); *A61K 45/06* (2013.01); *C07D 209/54* (2013.01)

(58) Field of Classification Search
CPC .............. A61K 31/343; A61K 31/4025; C07D 307/94; C07D 405/12; C07D 407/06; C07D 409/12
USPC ................... 514/409, 462; 548/407; 549/265
See application file for complete search history.

(56) References Cited

U.S. PATENT DOCUMENTS 9,211,333 B2 * 12/2015 Zhang .................... A61K 45/06

OTHER PUBLICATIONS

Jutiviboonsuk A, Zhang HJ, Tan GT, Ma CM, Hung NV, Cuong NM, Bunyapraphatsara N, Soejarto DD, Fong HHS. Bioactive constituents from the roots of Bursera tonkinensis. Phytochemistry 2005; 66: 2745-2751.
WHO: http://www.who.int/mediacentre/factsheets/fs297/en/; retrieved on Sep. 6, 2015.

* cited by examiner

*Primary Examiner* — Kristin Vajda
(74) *Attorney, Agent, or Firm* — Spruson & Ferguson (Hong Kong) Limited

(57) ABSTRACT

The present invention is in the field of pharmaceuticals and chemical industries. In particular, the present invention relates to new anticancer agents based on miliusane compounds. The present invention also includes its preparation and application method for treating cancer.

8 Claims, No Drawings

ANTICANCER MILIUSANE DERIVATIVES

CROSS-REFERENCE TO RELATED APPLICATIONS

The present application is a continuation-in-part application of U.S. non-provisional application Ser. No. 13/831,997 filed Mar. 15, 2013, which claims priority of U.S. provisional application No. 61/655,990 filed Jun. 5, 2012; and the disclosure of which are incorporated herein by reference by their entirety.

FIELD OF INVENTION

The present invention is in the field of pharmaceuticals and chemical industries. In particular, the present invention relates to anticancer agents based on miliusane compounds. The present invention also includes its preparation and application method for treating cancer.

BACKGROUND OF INVENTION

Cancer, in one form or another, is a leading cause of death, and claimed the lives of more than 8.2 million people worldwide in 2012, according to the compiled statistics by WHO (WHO: http://www.who.int/mediacentre/factsheets/fs297/en/; retrieved on Sep. 6, 2015). It is estimated that the annual cancer cases will reach 22 millions by 2036. Although numerous cancer chemotherapeutics are available today, they often have very narrow therapeutic indices and very severe side effects. In addition, cancers can and often do develop resistance to many of these drugs. The fact that there currently are no drugs available that are capable of curing cancer diseases, the discovery and development of new anticancer drugs are very much needed and the undertaking of such studies is imperative.

Miliusanes is a group of compounds containing a substructure of oxo-spirodecane. A few patents have been published related to the compounds containing oxospirodecane or azaspirodecane or thiaspirocecane substructure (US 2009/0318548A1; US2011/021624A1 and WO2011098433A1).

In US 2009/0318548A1, the compounds of formula (VI) are synthesized. However, no anticancer data is reported in this patent.

(VI)

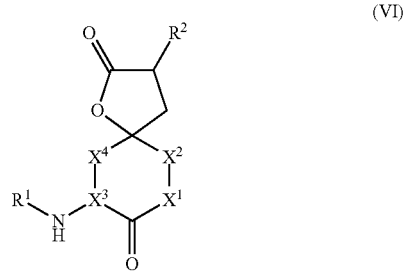

In US2011/021624A1, the compounds of formula (VII) are synthesized. However, the representative compound is reported to show weak cytotoxicity against MDA-MB-435, HCT116, A549 and Hela cancer cells ($IC_{50}$ values in the range of 17-42 µM).

(VII)

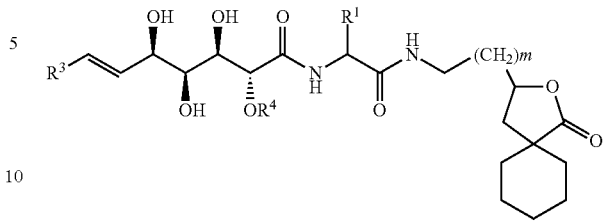

In WO2011098433A1, the compounds of formula (VIII) are synthesized. The compounds have a chemical structure containing a biphenyl group, and are reported to have tumor inhibition activity by inhibiting fatty acid synthesis.

(VIII)

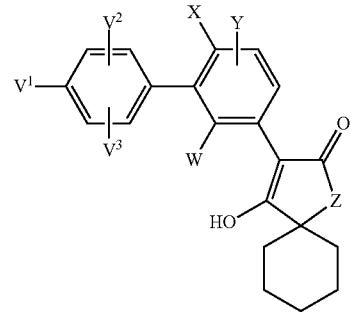

Thus, miliusanes compounds with more potent anticancer activity and low in toxicity are needed.

Citation or identification of any reference in this section or any other section of this application shall not be construed as an admission that such reference is available as prior art for the present application.

SUMMARY OF INVENTION

The present invention relates to anticancer compounds which are synthesized based on miliusane. More particularly, the compounds of the present invention are derivatives of the core structures of miliusanes. It is a goal of the present invention to provide miliusane derivatives having biological activity against cancer, particularly colon cancer, breast cancer, prostate cancer, lung cancer, melanoma, leukemia, brain cancer, renal cancer, ovarian cancer, and oral epidermoid cancer.

The present invention provides a series of novel anticancer compounds belonging to a cluster of molecules, referred herein to as "miliusanes", which are discovered from the leaves, twigs and flowers of *Miliusa sinensis* Finet and Gagnep. (Annonaceae) (Zhang H J, Ma C Y, Hung N V, Cuong N M, Tan G T, Santarsiero B D, Mesecar A D, Soejarto D D, Pezzuto J M, Fong H H S. Miliusanes, a class of cytotoxic agents from *Miliusa sinensis*. Journal of Medicinal Chemistry 2006; 49: 693-708). The series of anticancer compounds of the present invention are shown below:

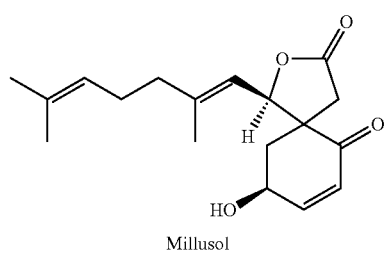

Miliusol

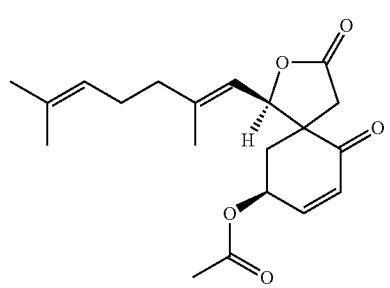

Miliusate

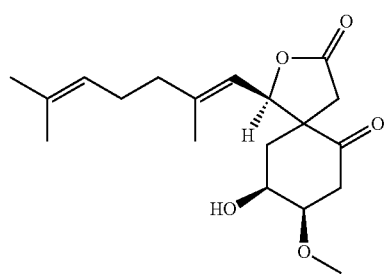

Miliusane I

The three miliusanes (miliusol, miliusate as well as miliusane I) are evaluated in the NCI 60 cell line panel. When using the NCI automated COMPARE analysis, it is observed that the three compounds displayed different $GI_{50}$ response patterns with those of the other compounds in the NCI database, indicating an unique anticancer mechanism of the miliusanes, which warranted the use of these miliusane compounds for cancer treatment.

U.S. patent application Ser. No. 13/931,997 discloses dozens of miliusane derivatives including N-methyl-2-pyrrolecarboxyl-miliusol and p-Dimethylamino-benzoyl-miliusol having the following structural formula:

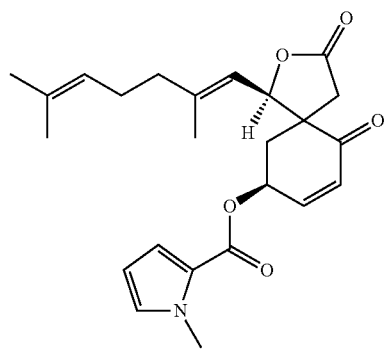

N-Methyl-2-pyrrolecarboxyl-miliusol

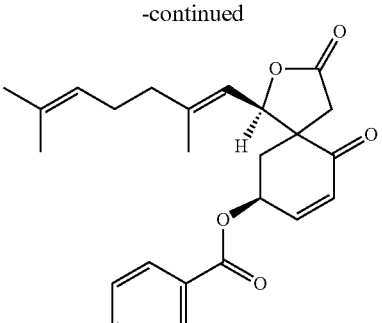

p-Dimethylamino-benzyol-miliusol

A first aspect of the present invention is a compound based on the core structures of miliusane for use in the treatment, prevention or delay of progression of a cancer in a patient.

A second aspect of the present invention is a pharmaceutically acceptable salt or prodrug based on the core structures of miliusane, for use in the treatment, prevention or delay of progression of a cancer in a patient.

A third aspect of the present invention is a pharmaceutical formulation comprising a compound based on the core structures of miliusane, or a pharmaceutically acceptable salt or prodrug thereof, for use in the treatment, prevention or delay of progression of a cancer in a patient.

Compounds of the present invention may exist in different forms, such as free acids, free bases, enantiomers, racemates, diastereomers, esters and other prodrugs, salts and tautomers, and the disclosure includes all variant forms of these compounds.

The extent of protection includes counterfeit or fraudulent products which contain or purport to contain a compound of the present invention irrespective of whether they do in fact contain such a compound and irrespective of whether any such compound is contained in a therapeutically effective amount.

Included in the scope of protection are packages which include a description or instructions which indicate that the package contains a species or pharmaceutical formulation of the present invention and a product which is or comprises, or purports to be or comprise, such a formulation or species. Such packages may be, but are not necessarily, counterfeit or fraudulent.

Features, integers, characteristics, compounds, chemical moieties or groups described in conjunction with a particular aspect, embodiment or example of the present invention are to be understood to be applicable to any other aspect, embodiment or example described herein unless incompatible therewith.

Those skilled in the art will appreciate that the present invention described herein is susceptible to variations and modifications other than those specifically described. The present invention includes all such variation and modifications. The present invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the present invention and apply throughout. Unless otherwise defined, all other technical terms used herein have the same meaning as commonly understood to one of ordinary skill in the art to which the present invention belongs.

Other aspects and advantages of the present invention will be apparent to those skilled in the art from a review of the ensuing description.

DETAILED DESCRIPTION OF INVENTION

The present invention is not to be limited in scope by any of the specific embodiments described herein. The following embodiments are presented for exemplification only.

Definitions

Miliusane and Core Structures

The term "miliusane" as used herein includes reference to a compound comprising the basic structure shown as below:

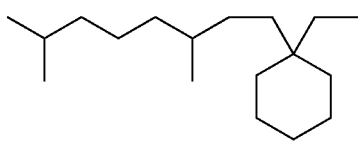

Miliusane

The carbon numbering of miliusane molecule as used herein includes reference to a compound comprising numbering system shown as below:

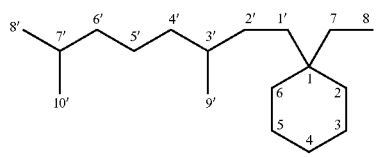

The term "the core structure of miliusane" as used herein includes reference to a compound comprising the basic structure shown as below:

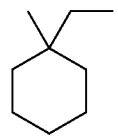

The core structure of miliusane

In one class of the core structures of miliusane compounds, the methyl group and the ethyl group form a tetrahydrofuran ring (1-oxa-spiro[4.5]decane and 2-oxa-spiro[4.5]decane).

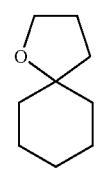 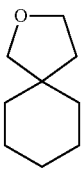

1-Oxa-spiro[4.5]decane    2-Oxa-spiro[4.5]decane

In the second class of the core structures of miliusane compounds, the methyl group and the ethyl group form a tetrahydro-thiophene ring (1-thia-spiro[4.5]decane and 2-thia-spiro[4.5]decane).

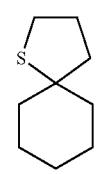 

1-Thia-spiro[4.5]decane    2-Thia-spiro[4.5]decane

In the third class of the cores structure of miliusane compounds, the methyl group and the ethyl group form a pyrrolidine ring (1-aza-spiro[4.5]decane, 2-aza-spiro[4.5]decane, 1-aza-spiro[4.5]dec-1-ene, 2-aza-spiro[4.5]dec-1-ene and 2-aza-spiro[4.5]dec-2-ene).

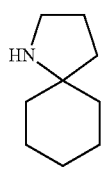 

1-Aza-spiro[4.5]decane    2-Aza-spiro[4.5]decane

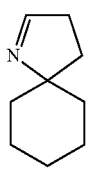 

1-Aza-spiro[4.5]dec-1-ene    2-Aza-spiro[4.5]dec-1-ene

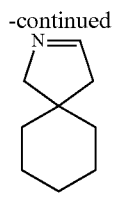

2-Aza-spiro[4.5]dec-2-ene

Hydrocarbyl

The term "hydrocarbyl" as used herein includes reference to a moiety consisting of hydrogen and carbon atoms; such a moiety may comprise an aliphatic and/or an aromatic moiety. The moiety may comprise 1, 2, 3, 4, 5, 6, 7, 8, 9, 10, 11, 12, 13, 14, 15, 16, 17, 18, 19 or 20 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g. benzyl) or by cycloalkyl (e.g. cyclopropylmethyl); cycloalkyl (e.g. cyclopropyl, cyclobutyl, cyclopentyl or cyclohexyl); aryl (e.g. phenyl, naphthyl or fluorenyl) and the like.

Alkyl

The terms "alkyl" and "$C_{1-6}$ alkyl" as used herein include reference to a straight or branched chain alkyl moiety having 1, 2, 3, 4, 5 or 6 carbon atoms. This term includes reference to groups such as methyl, ethyl, propyl (n-propyl or isopropyl), butyl (n-butyl, sec-butyl or tert-butyl), pentyl, hexyl and the like. In particular, the alkyl moiety may have 1, 2, 3 or 4 carbon atoms.

Alkenyl

The terms "alkenyl" and "$C_{2-6}$ alkenyl" as used herein include reference to a straight or branched chain alkyl moiety having 2, 3, 4, 5 or 6 carbon atoms and having, in addition, at least one double bond, of either E or Z stereochemistry where applicable. This term includes reference to groups such as ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like.

Alkynyl

The terms "alkynyl" and "$C_{2-6}$ alkynyl" as used herein include reference to a straight or branched chain alkyl moiety having 2, 3, 4, 5 or 6 carbon atoms and having, in addition, at least one triple bond. This term includes reference to groups such as ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl and 3-hexynyl and the like.

Alkoxy

The terms "alkoxy" and "$C_{1-6}$ alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Cycloalkyl

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

Aryl

The term "aryl" as used herein includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic. This term includes reference to groups such as phenyl, naphthyl, fluorenyl, azulenyl, indenyl, anthryl and the like.

Cyclic Group

"Cyclic group" means a ring or ring system, which may be unsaturated or partially unsaturated but is usually saturated, typically containing 5 to 13 ring-forming atoms, for example a 5- or 6-membered ring. The ring or ring system may be substituted with one or more hydrocarbyl groups. Cyclic group includes carbocyclyl and heterocyclyl moieties.

Carbocyclyl

The term "carbocyclyl" as used herein includes reference to a saturated (e.g. cycloalkyl) or unsaturated (e.g. aryl) ring moiety having 3, 4, 5, 6, 7, 8, 9, 10, 11, 12, 13, 14, 15 or 16 carbon ring atoms. In particular, carbocyclyl includes a 3- to 10-membered ring or ring system and, in particular, 5- or 6-membered rings, which may be saturated or unsaturated. The ring or ring system may be substituted with one or more hydrocarbyl groups. A carbocyclic moiety is, for example, selected from cyclopropyl, cyclobutyl, cyclopentyl, cyclohexyl, norbornyl, bicyclo[2.2.2]octyl, phenyl, naphthyl, fluorenyl, azulenyl, indenyl, anthryl and the like.

Heterocyclyl

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9, 10, 11, 12, 13, 14, 15 or 16 ring atoms, at least one of which is selected from nitrogen, oxygen, phosphorus, silicon and sulphur. In particular, heterocyclyl includes a 3- to 10-membered ring or ring system and more particularly a 5- or 6-membered ring, which may be saturated or unsaturated. The ring or ring system may be substituted with one or more hydrocarbyl groups.

A heterocyclic moiety is, for example, selected from oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, pyrrolizidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4/V-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazoiyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl and the like.

Heterocycloalkyl

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like. The ring or ring system may be substituted with one or more hydrocarbyl groups.

Heteroaryl

The term "heteroaryl" as used herein includes reference to an aromatic heterocyclic ring system having 5, 6, 7, 8, 9, 10, 11, 12, 13, 14, 15 or 16 ring atoms, at least one of which is selected from nitrogen, oxygen and sulphur. The group may be a polycyclic ring system, having two or more rings, at least one of which is aromatic, but is more often monocyclic. The ring or ring system may be substituted with one or more hydrocarbyl groups. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

Halogen

The term "halogen" as used herein includes reference to F, Cl, Br or I.

Halogen Containing Moiety

The expression "halogen containing moiety" as used herein includes reference to a moiety comprising 1 to 30 plural valence atoms selected from carbon, nitrogen, oxygen and sulphur which moiety includes at least one halogen. The moiety may be hydrocarbyl for example $C_{1-6}$ alkyl or $C_{1-6}$ alkoxy, or carbocyclyl for example aryl.

Substituted

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or un-substituted. It will, of course, be understood that substituents are only at positions where they are chemically possible, the person skilled in the art being able to decide (either experimentally or theoretically) without inappropriate effort whether a particular substitution is possible.

Enantiomer

The term "enantiomer" as used herein means one of two stereoisomers that have mirror images of one another.

Racemate

The term "racemate" as used herein means a mixture of equal amounts of enantiomers of a chiral molecule.

Diastereomer

The term "diastereomer" as used herein means one of a class of stereoisomers that are not enantiomers, but that have different configurations at one or more of the equivalent chiral centers. Example of diasteromers are epimers that differ in configuration of only one chiral center.

Stereoisomer

The term "stereoisomer" as used herein means one of a class of isomeric molecules that have the same molecular formula and sequence of bonded atoms, but different three-dimensional orientations of their atoms in space.

Tautomers

The term "tautomer" means isomeric molecules that readily interconvert by a chemical reaction. The reaction commonly results in the migration of a hydrogen atom, which results in a switch of a single bond and adjacent double bond.

Prodrug

A prodrug is a medication that is administered as an inactive (or less than fully active) chemical derivative that is subsequently converted to an active pharmacological agent in the body, often through normal metabolic processes.

Independently

Where two or more moieties are described as being "each independently" selected from a list of atoms or groups, this means that the moieties may be the same or different. The identity of each moiety is therefore independent of the identities of the one or more other moieties.

Embodiments of the present invention are described below. Preferred features of each aspect of the present invention are as for each of the other aspects mutatis mutandis. Moreover, it will be appreciated that the features specified in each embodiment may be combined with other specified features, to provide further embodiments.

Compounds of the Present Invention

In an exemplary embodiment, the present invention provides compounds of formula (I), or (II):

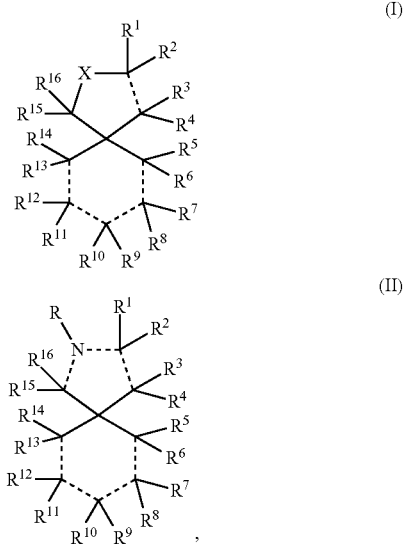

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are each independently selected from hydrogen, halogen or a moiety comprising 1 to 30 plural valence atoms selected from carbon, nitrogen, oxygen and sulphur; or these groups may be taken together with the carbon atoms to which they are attached to form one or more cyclic groups which is optionally substituted with halogen or a moiety comprising 1 to 30 plural valence atoms selected from carbon, nitrogen, oxygen and sulphur; $R^1$ and $R^2$, $R^3$ and $R^4$, $R^5$ and $R^6$, $R^7$ and $R^8$, $R^9$ and $R^{10}$, $R^{11}$ and $R^{12}$, $R^{13}$ and $R^{14}$ or $R^{15}$ and $R^{16}$ may be taken together with the carbon atoms to which they are attached to form one or more carboxyl groups (C=O); or while one of $R^1$ and $R^2$, $R^3$ and $R^4$, $R^5$ and $R^6$, $R^7$ and $R^8$, $R^9$ and $R^{10}$, $R^{11}$ and $R^{12}$, $R^{13}$ and $R^{14}$ or $R^{15}$ and $R^{16}$ is hydrogen, halogen, hydrocarbyl or alkoxy, the other one of $R^1$ and $R^2$, $R^3$ and $R^4$, $R^5$ and $R^6$, $R^7$ and $R^8$, $R^9$ and $R^{10}$, $R^{11}$ and $R^{12}$, $R^{13}$ and $R^{14}$ or $R^{15}$ and $R^{16}$ is selected from $R^{17}$, —$OR^{17}$, —$C(O)R^{17}$ and —$C(O)OR^{17}$; $R^{17}$ is independently selected from hydrogen, halogen, trifluoromethyl, cyano, nitro, hydrocarbyl optionally substituted with 1, 2, 3, 4 or 5 $R^{18}$, —$(CH_2)_k$-heterocyclyl optionally substituted with 1, 2, 3, 4 or 5 $R^{18}$, —$OR^{19}$, —$C(O)R^{20}$, —$C(O)N(R^{19})R^{20}$, $C(O)OR^{19}$, —$OC(O)R^{19}$, —$S(O)_2R^{19}$, —$S(O)_2N(R^{19})R^{20}$, —$N(R^{19})R^{20}$, —$N(R^{19})N(R^{19})R^{20}$, —$N(R^{19})C(O)R^{20}$ and —$N(R^{19})S(O)_2R^{20}$;

wherein k is an integer between 1 and 6 (e.g. 1, 2 or 3); $R^{18}$ is independently selected from halogen, trifluoromethyl, cyano, nitro, oxo, =$NR^{19}$, —$OR^{19}$, —$C(O)R^{20}$, —$C(O)N(R^{19})R^{20}$, —$C(O)OR^{19}$, —$OC(O)R^{20}$, —$S(O)_2R^{19}$, —$S(O)_2N(R^{19})R^{20}$, —$N(R^{19})R^{20}$, —$N(R^{19})N(R^{19})R^{20}$, —$N(R^{19})C(O)R^{20}$ and —$N(R^{19})S(O)_2R^{20}$; $R^{19}$ and $R^{20}$ are each independently hydrogen or selected from hydrocarbyl and —$(CH_2)_k$-heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy; wherein k is an integer between 1 and 6 (e.g. 1, 2 or 3); X is oxygen or sulphur; R is hydrogen or selected from hydrocarbyl and —$(CH_2)_k$-heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy; wherein k is an integer between 1 and 6 (e.g. 1, 2 or 3); dashed line "----" denotes a single or double bond; or an enantiomer thereof; or a pharmaceutically acceptable salt or prodrug thereof.

The present invention also provides pharmaceutical composition comprises compound of the present invention and pharmaceutical acceptable carrier thereof.

It should be noted that compounds having one of the following formulae should not be the compound of the present invention and should be removed from the compound of the present invention:

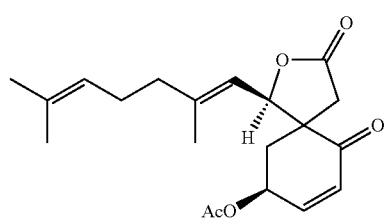

Miliusate

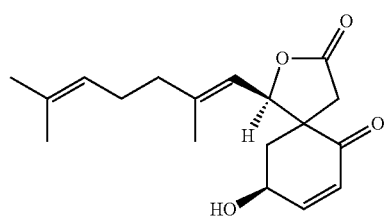

Miliusol

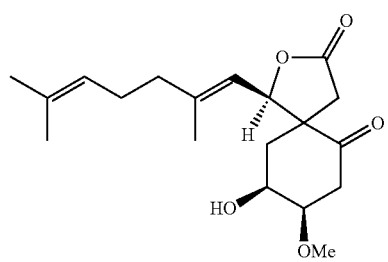

Miliusane I

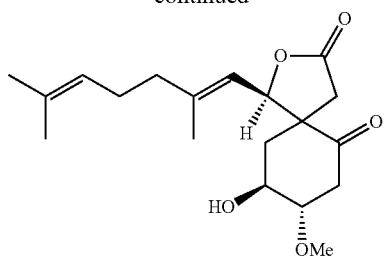

Miliusane II

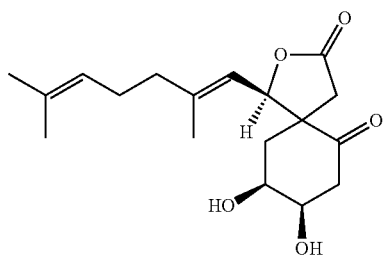

Miliusane III

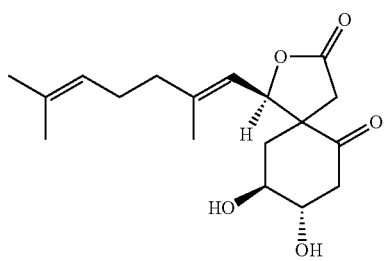

Miliusane IV

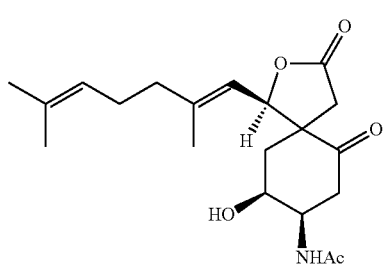

Miliusane V

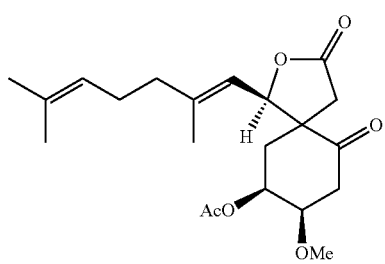

Miliusane VI

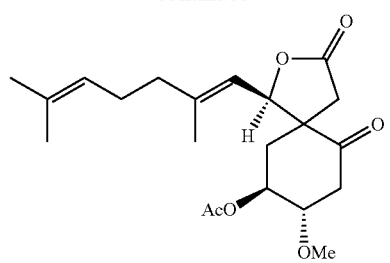
Miliusane VII
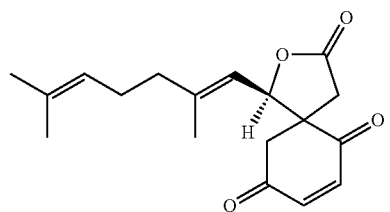
Miliusane VIII
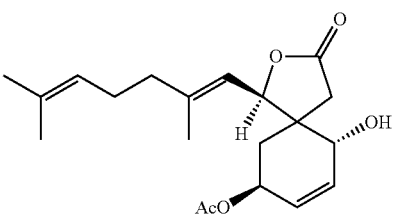
Miliusane IX
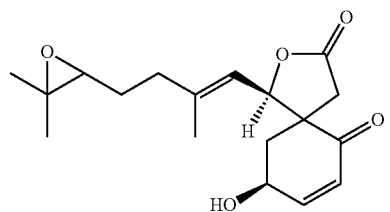
Miliusane X/XI
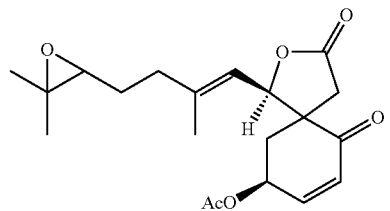
Miliusane XII/XIII
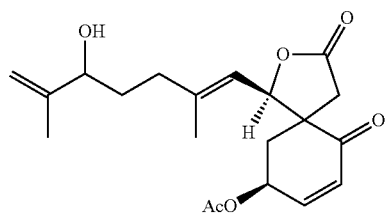
Miliusane XIV/XV
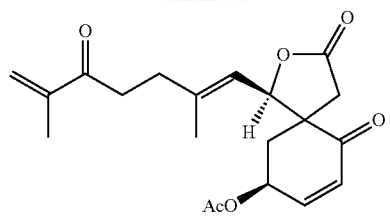
Miliusane XVI
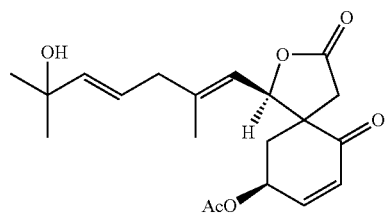
Miliusane XVII
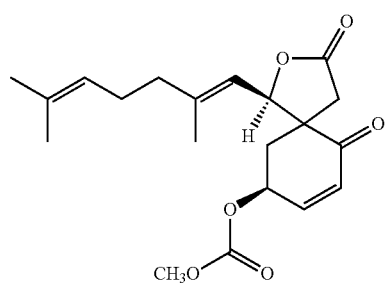
Methoxyacetyl-miliusol
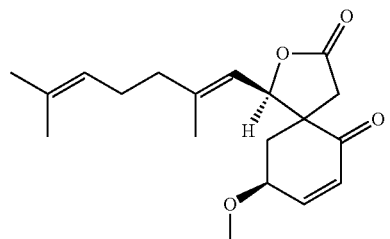
n-Hexanoyl-miliusol
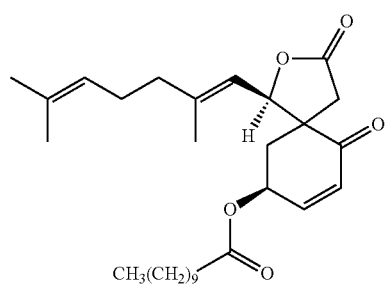
Undecanoyl-miliusol -continued

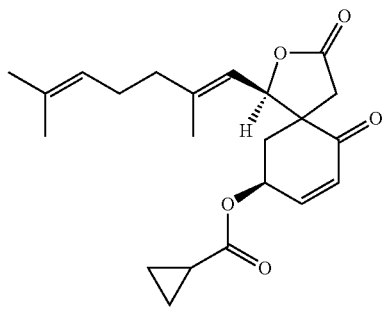

Cyclopropanecarbonyl-miliusol

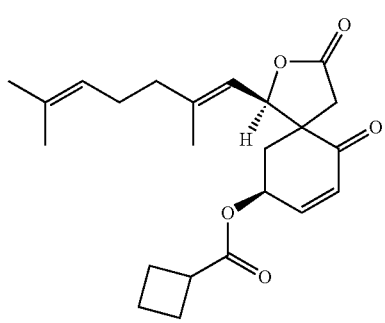

Cyclobutanecarbonyl-miliusol

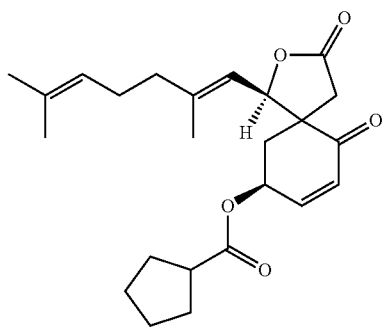

Cyclopentanecarbonyl-miliusol

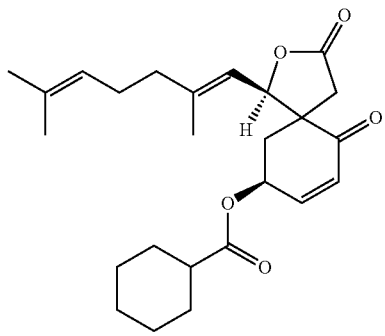

Cyclohexanecarbonyl-miliusol

-continued

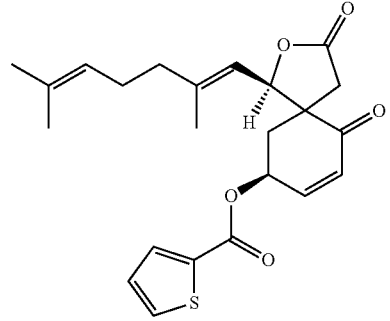

2-Thiophenecarbonyl-miliusol wherein Ac is acetyl group ($CH_3C=O$), and Me is methyl group ($CH_3$);

Compounds having the following formula (V) are excluded in the present invention:

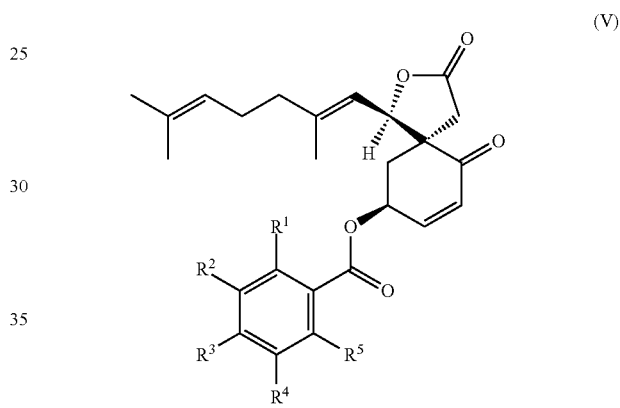

(V)

wherein $R^1=R^2=R^3=R^4=R^5=H$; or $R^1=R^2=R^3=R^4=H$, $R^5=OCH_3$; or $R^1=R^3=R^4=R^5=H$, $R^2=OCH_3$; or $R^1=R^2=R^4=R^5=H$, $R^3=OCH_3$; or $R^1=R^2=R^4=H$, $R^3=R^5=OCH_3$; or $R^1=R^5=OCH_3$, $R^2=R^3=R^4=H$; or $R^1=R^4=R^5=H$, $R^2=R^3=OCH_3$; or $R^1=R^3=R=H$, $R^2=R^4=OCH_3$; or $R^1=H$, $R^2=R^3=R^4=OCH_3$; or $R^1=R^4=R^5=H$, $R^2$ and $R^3$ taken together with the carbon atoms to which they are attached to form a cyclic[1,3] dioxole group; or $R^1=R^2=R^3=R^4=H$, $R^5=CH_3$; or $R^1=R^3=R^4=R^5=H$, $R^2=CH_3$; or $R^1=R^2=R^4=R^5=H$, $R^3=CH_3$; or $R^1=R^2=R^3=R^4=H$, $R^5=F$; or $R^1=R^3=R^4=R^5=H$, $R^2=F$; or $R^1=R^2=R^4=R^5=H$, $R^3=F$; or $R^1=R^2=R^3=H$, $R^4=R^5=F$; or $R^1=R^2=R^4=H$, $R^3=R^5=F$; or $R^1=R^3=R^4=H$, $R^2=R^5=F$; or $R^1=R^5=F$, $R^2=R^3=R^4=H$; or $R^1=R^4=R^5=H$, $R^2=R^3=F$; or $R^1=R^3=R^5=H$, $R^2=R^4=F$; or $R^1=R^2=R^3=R^4=H$, $R^5=Cl$; or $R^1=R^3=R^4=R=H$, $R^2=Cl$; or $R^1=R^2=R^4=R=H$, $R^3=Cl$; or $R^1=R^2=R^4=H$, $R^3=R^5=Cl$; or $R^1=R^5=Cl$, $R^2=R^3=R^4=H$; or $R^1=R^4=R^5=H$, $R^2=R^3=Cl$; or $R^1=R^3=R^5=H$, $R^2=R^4=Cl$; or $R^1=R^2=R^3=R^4=H$, $R^5=Br$; or $R^1=R^3=R^4=R^5=H$, $R^2=Br$; or $R^1=R^2=R^4=R^5=H$, $R^3=Br$; or $R^1=R^2=R^3=R^4=H$, $R^5=I$; or $R^1=R^2=R^4=R^5=H$, $R^3=I$;

Compounds having the following formula (VI) are excluded in the present invention:

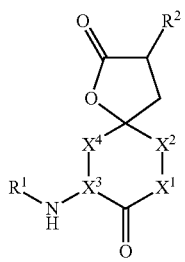

(VI)

wherein $X^1$ and $X^2$ are carbon atoms either joined by double bond or joined by a single bond constituents of an epoxide ring or a hydroxyethylene moiety; $X^3$ and $X^4$ are carbon atoms either joined by double bond or joined by a single bond constituents of an epoxide ring or a hydroxyethylene moiety; $R^1$ is selected from the group consisting of branched alkyl chains, unbranched alkyl chains, cycloalkyl groups, aromatic groups, alcohols, ethers, amines, and substituted or unsubstituted ureas, esters, aldehydes and carboxylic acids; $R^2$ is selected from the group consisting of H, OH and $NHR^3$, wherein $R^3$ is a nitrogen protecting group;

Compounds having the following formula (VII) are excluded in the present invention:

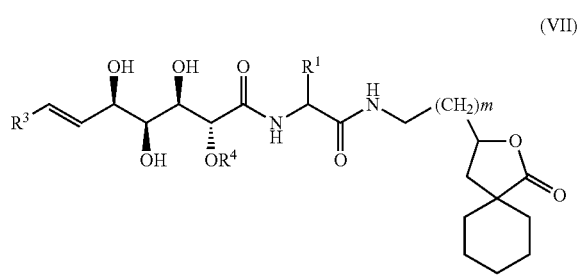

(VII)

wherein $R^1$, $R^3$ and $R^4$ are selected from the group consisting of branched alkyl chains, unbranched alkyl chains, cycloalkyl groups, aromatic groups, alcohols, ethers, amines, and substituted or unsubstituted ureas, esters, aldehydes and carboxylic acids; m is an integer between 0 and 5;

Compounds having the following formula (VIII) are excluded in the present invention:

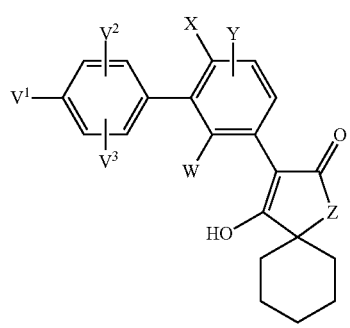

(VIII)

wherein Z is oxygen or sulphur or nitrogen substituted with D group; D represents hydrogen or represents a $C_1$-$C_6$-alkyl or $C_1$-$C_6$-alkoxy-$C_1$-$C_6$-alkyl radical or represents a $C_3$-$C_7$-cycloalkyl or 4- to 7-membered monocyclic heterocyclyl radical, where the radicals mentioned may optionally be mono- or polysubstituted by identical or different substituents selected from the group consisting of halogen and hydroxyl and $C_1$-$C_3$-alkyl, halo-$C_1$-$C_3$-alkyl, or $C_1$-$C_3$-alkoxy; X represents halogen, nitro or cyano or represents an optionally monohalogen- or polyhalogen-substituted $C_1$-$C_6$-alkyl, $C_1$-$C_6$-alkoxy, $C_1$-$C_6$-alkoxy-$C_1$-$C_6$-alkoxy, $C_3$-$C_7$-cycloalkyl or a $C_3$-$C_7$-cycloalkyl-$C_1$-$C_6$-alkoxy radical, and W and Y independently of one another represent hydrogen, nitro, cyano or halogen or represent an optionally monohalogen- or polyhalogen-substituted $C_1$-$C_6$-alkyl, $C_1$-$C_6$-alkoxy or $C_3$-$C_7$-cycloalkyl radical, and $V^1$, $V^2$ and $V^3$ independently of one another represent hydrogen, halogen, nitro or cyano or represent a $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, $C_1$-$C_6$-alkylsulphinyl, $C_1$-$C_6$-alkylsulphonyl, $C_1$-$C_6$-alkoxy-$C_1$-$C_6$-alkyl, $C_3$-$C_{10}$-Cycloalkyl radical or represent a monocyclic heterocycloalkyl radical, and/or $V^1$ and $V^2$ together with the carbon atoms to which they are attached form a saturated or unsaturated cycle $T^1$ which optionally contains at least one further heteroatom and has 4 to 7-ring atoms and whose ring-forming atoms may be mono- or polysubstituted by identical or different substituents selected from the group consisting of halogen and a $C_1$-$C_6$-alkyl radical.

Examples of the compounds of the present invention include those shown below. It will of course be appreciated that, where appropriate, each compound may be in the form of the free compound, an enantiomer, an acid or base addition salt, or a prodrug.

The present invention provides 17 compounds with potent anti-cancer activity and synthesis thereof. The compounds of the present invention are synthesized and evaluated for their anticancer activity, namely 4β-(N-phenyl)miliusate, 4α-(N-phenyl)miliusate, 4β-(N-benzoyl-N-phenyl)miliusate, 4α-(N-benzoyl-N-phenyl)miliusate, hexahydro-miliusate, 3,4-dihydro-miliusate, 2', 3',6',7'-tetrahydro-miliusate, 2-hydroxy-3,4-dihydro-miliusate, 2-acetoxy-3,4-dihydro-miliusate, 8'-oxo-miliusate, 8'-hydroxy-miliusate, 10'-hydroxy-8'-oxo-miliusate, 8',10'-dihydroxy-miliusate, 5β-(p-trimethylammonio-benzoyl)miliusol iodide, 5β-(p-dimethyl-allyl-ammonio-benzoyl)miliusol bromide, N-(n-butyl)-miliusol lactam and N-phenyl-miliusol lactam. The chemical formulae of the compound of the present invention are as follows:

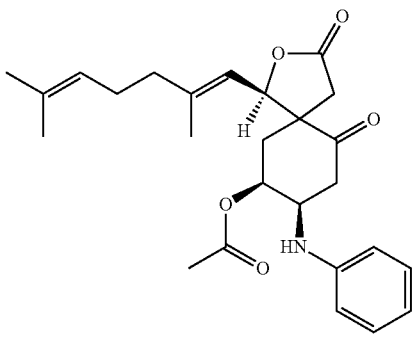

4β-(N-Phenyl)miliusate

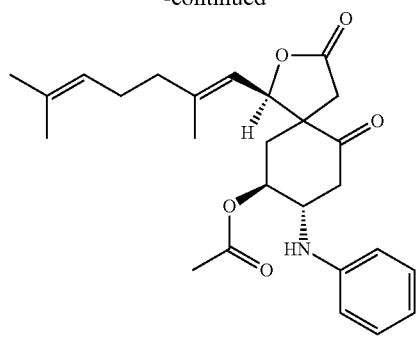
4α-(N-Phenyl)miliusate
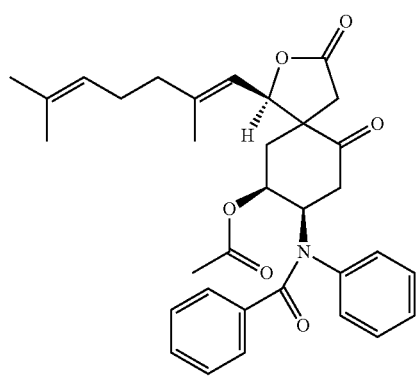
4β-(N-Benzoyl-N-phenyl)miliusate
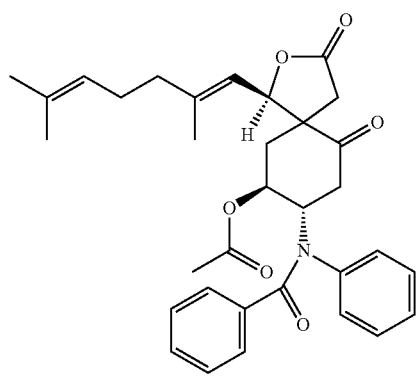
4α-(N-Benzoyl-N-phenyl)miliusate
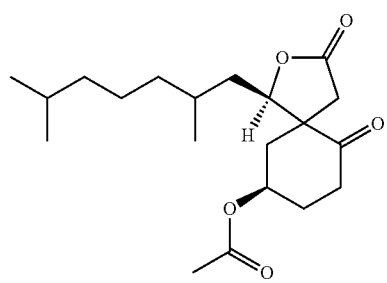
Hexahydro-miliusate
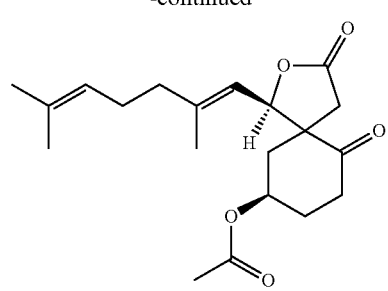
3, 4 -Dihydro-miliusate
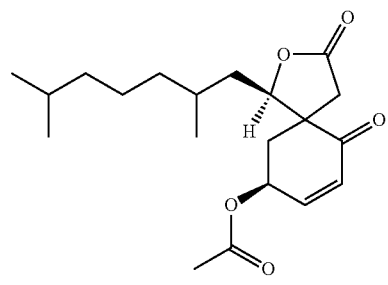
2', 3', 6', 7'-Tetrahydro-miliusate
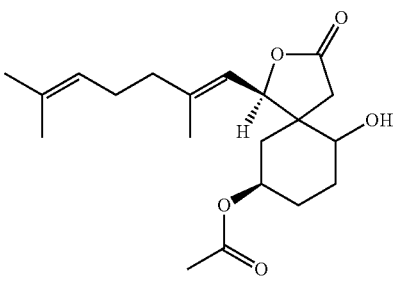
2-Hydroxy-3, 4-dihydro-miliusate
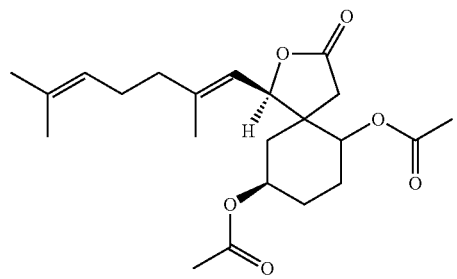
2-Acetoxy-3, 4-dihydro-miliusate
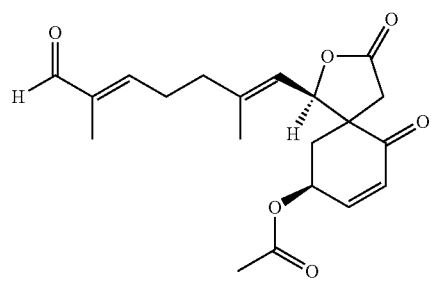
8'–Oxo-miliusate -continued

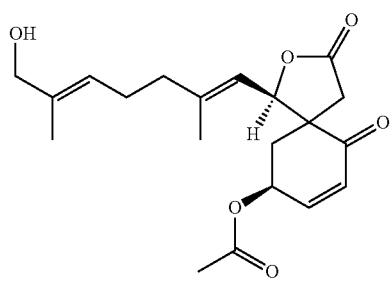

8′-Hydroxy-miliusate

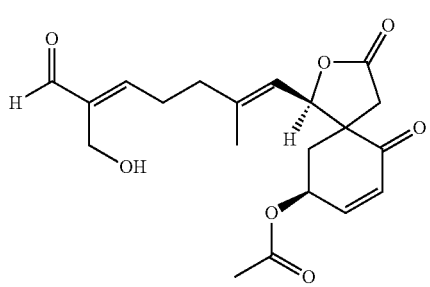

10′-Hydroxy-8′-oxo-miliusate

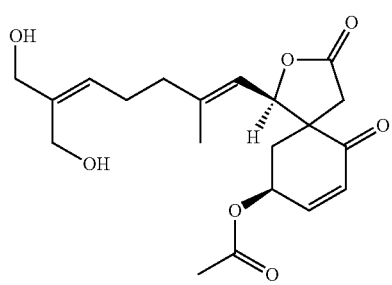

8′,10′-Dihydroxy-miliusate

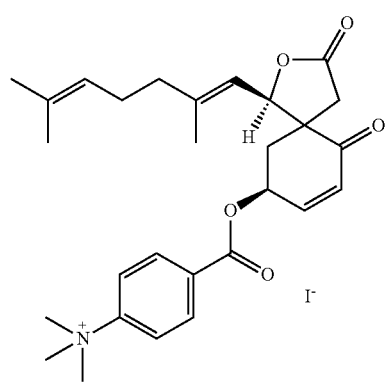

5β-(p-Trimethylammonio-benzyol)miliusol iodide

-continued

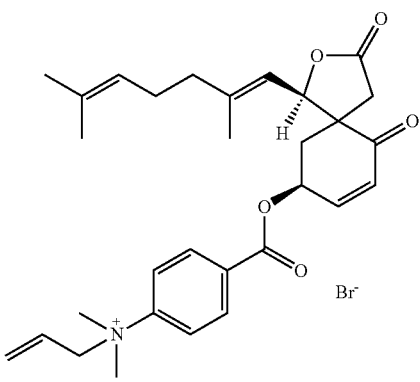

5β-(p-Dimethyl-allyl-ammonio-benzyol)miliusol bromide

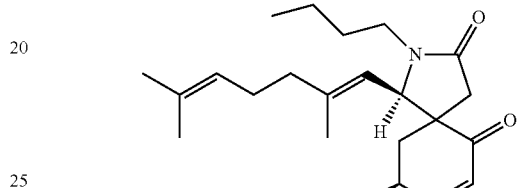

N-(n-Butyl)-miliusol lactam

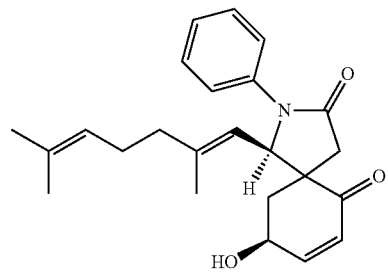

N-Phenyl-miliusol lactam

EXAMPLES

Synthesis of Novel Miliusane Derivatives. The two natural miliusane compounds (miliusol and miliusate), isolated from *Miliusa balansae* Finet & Gagnep. (Annonaceae), were used as the starting compounds to prepare new miliusane derivatives. By using different synthetic methods, 17 new miliusane analogues are synthesized.

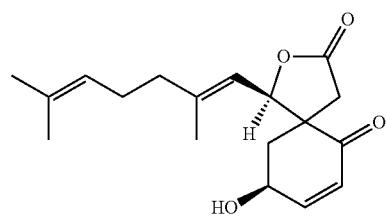

Miliusol

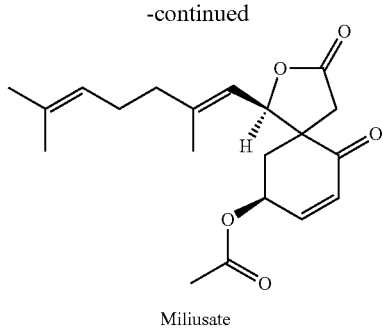

Miliusate

These new miliusane compounds have been evaluated for their anticancer activity against a panel of cancer cell lines comprising KB, HCT116, LNCaP, A549, MCF-7 and A375. 4β-(N-Phenyl)miliusate demonstrates cell killing activity with $IC_{50}$ values ranging from 0.2-2.0 µM. 4α-(N-Phenyl) miliusate demonstrated cell killing activity with $IC_{50}$ values ranging from 1.1-6.5 µM. 4β-(N-Benzoyl-N-phenyl)miliusate demonstrates cell killing activity with $IC_{50}$ values ranging from 0.5-2.5 µM. 4α-(N-Benzoyl-N-phenyl)miliusate demonstrates cell killing activity with $IC_{50}$ values ranging from 5.0-9.8 µM. 2',3',6',7'-Tetradehydro-miliusate demonstrates cell killing activity with $IC_{50}$ values ranging from 1.2-6.8 µM. 8'-Oxo-miliusate demonstrates cell killing activity with $IC_{50}$ values ranging from 3.6-5.5 µM. 8'-Hydroxy-miliusate demonstrates cell killing activity with $IC_{50}$ values ranging from 4.2-8.9 µM. 10'-Hydroxy-8'-oxo-miliusate demonstrates cell killing activity with $IC_{50}$ values ranging from 2.5-4.9 µM. 5β-(p-Trimethylammonio-benzoyl)miliusol iodide demonstrates cell killing activity with $IC_{50}$ values ranging from 0.05-1.2 µM. 5β-(p-Dimethylallyl-ammonio-benzoyl)miliusol bromide demonstrates cell killing activity with $IC_{50}$ values ranging from 0.1-1.5 µM. N-(n-Butyl)-miliusol lactam demonstrates cell killing activity with $IC_{50}$ values ranging from 0.5-4.2 µM. 5β-(p-Trimethylammonio-benzoyl)miliusol iodide, 5β-(p-dimethyl-allyl-ammonio-benzoyl)miliusol bromide, and 4β-(N-phenyl)miliusate demonstrate more potent cell killing activity than that of miliusol. All other compounds show no cell killing activity at a concentration of 20 µM.

Since 4β-(N-phenyl)miliusate shows better cell killing activity than that of miliusol in the in vitro evaluation system, the compound is further evaluated for its in vivo antitumor activity in HCT116 xenograft mouse model study. In the experiment, HCT116 tumors in mice treated with 4β-(N-phenyl)miliusate grow much slower than those mice treated with vehicle. After 21 days administration, the measured average tumor size (L×W×W) is suppressed by 30.5% with treatment of 4β-(N-phenyl)miliusate at the dose of 20 mg/kg (p<0.01) in comparison with the vehicle control group (paclitaxel, the clinically used anticancer drug, shows 23.3% inhibition of tumor growth at the dose of 10 mg/kg). In addition, no weight loss is observed for the mice in the 4β-(N-phenyl)miliusate treatment group. On the contrary, 3 out of 10 mice died for the paclitaxel group. These results clearly indicate the superior antitumor efficacy of 4β-(N-phenyl)miliusate with low toxicity in comparison with the clinically used drug paclitaxel.

General Method for Preparation of 4-Amino Substituted Miliusane Derivatives. Bismuth nitrate [Bi(NO$_3$)$_3$] (70 mg, 0.5 eq) is added to a mixture of an amine such as aniline (1.35 g, 50 eq) and a miliusane such as miliusate (100 mg, 0.29 mmol) in dichloromethane (CH$_2$Cl$_2$, 2 mL). The reaction mixture is stirred at room temperature for 48 hours. CH$_2$Cl$_2$ (30 mL) is added to the reaction mixture, and the CH$_2$Cl$_2$ solution is filtered through filter paper to remove Bi(NO$_3$)$_3$. The filtrate is washed with saturated NaHCO$_3$ (2×10 mL) and brine (1×10 mL), and dried over in Na$_2$SO$_4$. The CH$_2$Cl$_2$ solution is concentrated, and is further purified using chromatography on a silica gel column eluting with a mixture of solvent such as petroleum ether: EtOAc (ethyl acetate) 4:1 to afford 4-amino substituted miliusane derivative(s). Unreacted, partially reacted or unwanted compounds as disclosed herein should be removed from the reaction product.

SCHEME 1

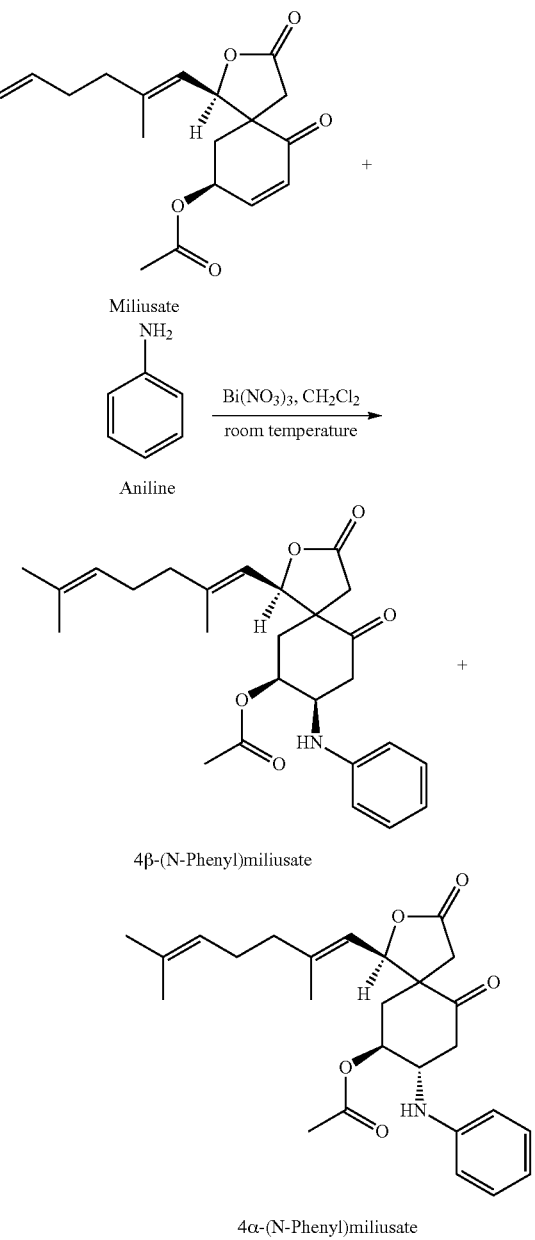

The new molecules 4β-(N-phenyl)miliusate and 4α-(N-phenyl)miliusate are thus synthesized (see Scheme 1).

General Method for Preparation of Amino Substituted Miliusane Amide Derivatives. To a solution of an amino substituted miliusane derivative such as 4α-(N-benzyl)miliusate and 4β-(N-benzyl)miliusate (30 mg, 0.068 mmol) in anhydrous pyridine (5 mL) is added benzoyl chloride (BzCl) (19 mg, 2 eq) and catalytic amount of 4-dialkylaminopyridine (DMAP). The reaction is stirred overnight at room temperature, and quenched with $H_2O$ (30 mL). The reaction mixture is then extracted with ethyl acetate (3×20 mL). The combined ethyl acetate solution is washed with $H_2O$ (20 mL) and brine (20 mL), and dried with $Na_2SO_4$. The solution is then concentrated in vacuo, and chromatographed on a silica gel column, eluted with a solvent system such as petroleum ether: EtOAc 2:1 to afford amino substituted miliusane amide derivative. Unreacted, partially reacted or unwanted compounds as disclosed herein should be removed from the reaction product.

SCHEME 2

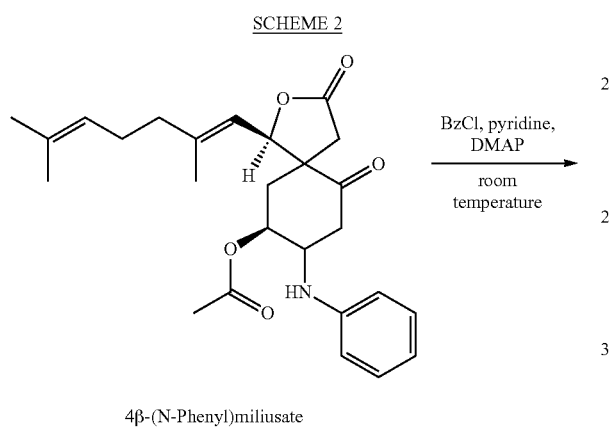

4β-(N-Phenyl)miliusate

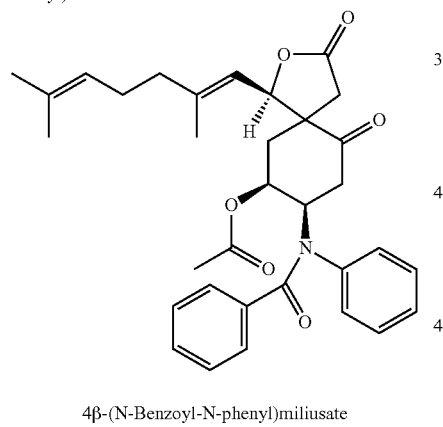

4β-(N-Benzoyl-N-phenyl)miliusate

SCHEME 3

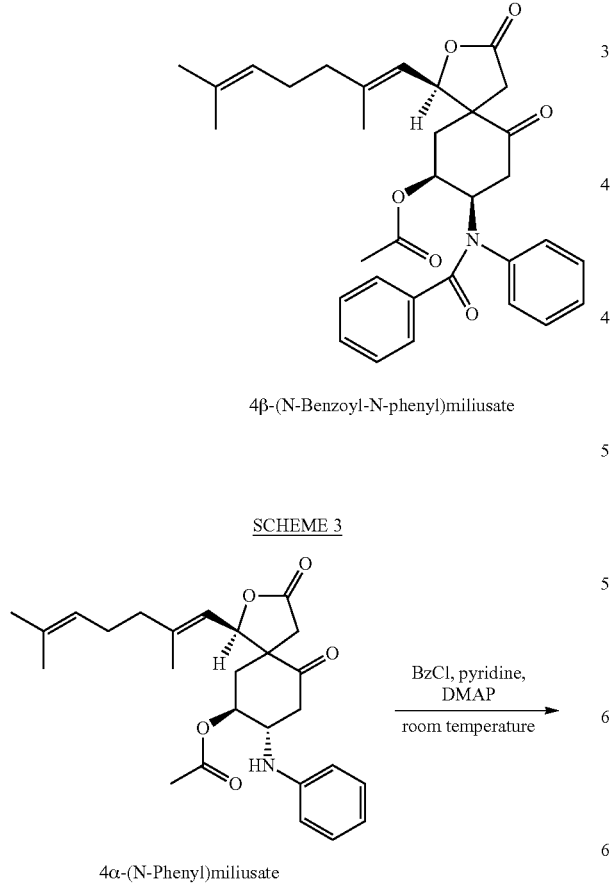

4α-(N-Phenyl)miliusate

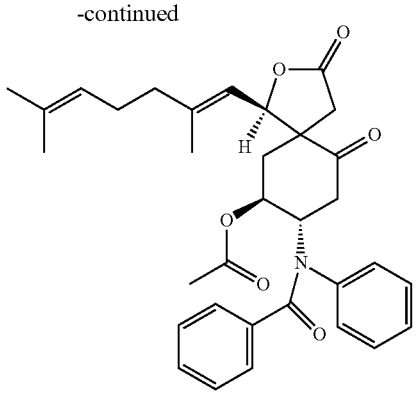

4α-(N-Benzoyl-N-phenyl)miliusate

The new molecules 4β-(N-benzoyl-N-phenyl)miliusate, and 4α-(N-benzoyl-N-phenyl)miliusate are thus synthesized (see Schemes 2 and 3).

General Method for Preparation of Hexahydro-Miliusane Derivatives. A solution of a miliusane such as miliusate (20 mg, 0.058 mmol) in EtOAc (5 mL) is treated with 10% of the catalyst palladium on activate charcoal (Pd/C) (5 mg). The resulting black suspension is stirred under hydrogen ($H_2$) (1 atmosphere) at room temperature for 3 hours. The catalyst is removed by filtration through Celite and washed with EtOAc (20 mL). The filtrate is evaporated in vacuo and the residue is subjected to chromatography separation on silica gel, eluted with a solvent system such as petroleum ether: EtOAc 4:1 to afford hexahydro-miliusane derivative. Unreacted, partially reacted or unwanted compounds as disclosed herein should be removed from the reaction product.

SCHEME 4

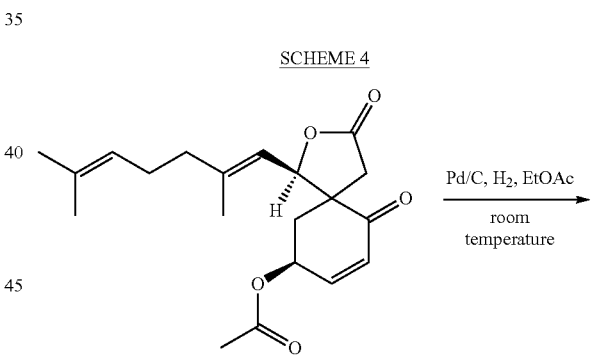

Miliusate

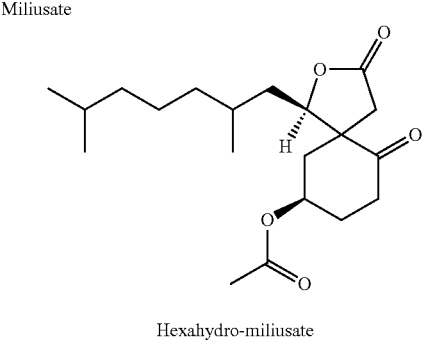

Hexahydro-miliusate

The new molecule hexahydro-miliusate is thus synthesized (see Scheme 4).

General Method for Preparation of 3,4-Dihydro-Miliusane Derivatives. A solution of a miliusane such as miliusate (10 mg, 0.029 mmol) in EtOAc (3 mL) is treated with 10%

Pd/C (5 mg). The resulting black suspension is stirred under H₂ (1 atmosphere) at −78° C. for 48 hours. The catalyst is removed by filtration through Celite and washed with EtOAc (20 mL). The filtrate is evaporated in vacuo and the residue is subjected to chromatography separation on silica gel, eluted with a solvent system such as petroleum ether: EtOAc 4:1 to afford 3,4-dihydro-miliusane derivative. Unreacted, partially reacted or unwanted compounds as disclosed herein should be removed from the reaction product.

SCHEME 5

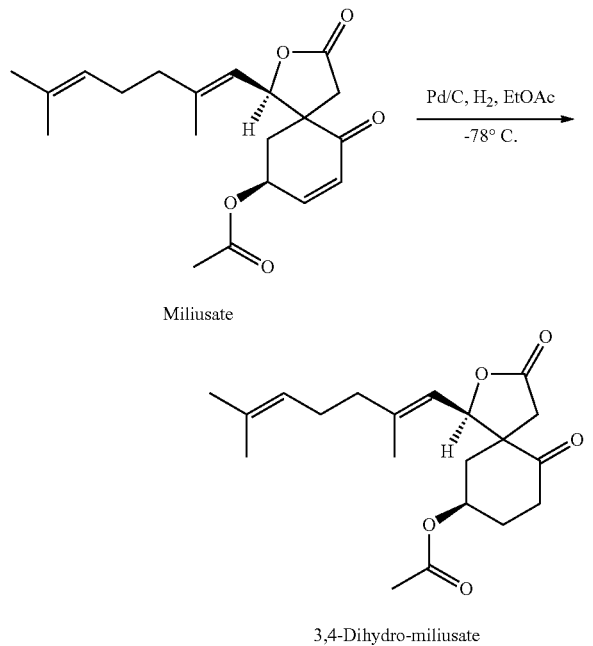

3,4-Dihydro-miliusate

The new molecule 3,4-dihydro-miliusate is thus synthesized (see Scheme 5).

General Method for Preparation of 2′,3′,6′,7′-Tetrahydro-Miliusane Derivatives. To a solution of a miliusane such as hexahydro-miliusate (20 mg, 0.056 mmol) in toluene: DMSO (2:1, 0.1 M) is added 2-iodoxybenzoic acid (IBX) (20.7 mg, 1.3 eq). The resulting solution is heated to 100° C. for stirring 3 hours. The reaction mixture is then diluted with CH₂Cl₂ (30 mL), and washed sequentially with 5% NaHCO₃ (1×10 mL), H₂O (1×10 mL), and brine (1×10 mL), followed by removal of solvent in vacuo, leading to crude products, which can be purified using silica gel column chromatography to afford 2′,3′,6′,7′-tetrahydro-miliusane derivative. Unreacted, partially reacted or unwanted compounds as disclosed herein should be removed from the reaction product.

SCHEME 6

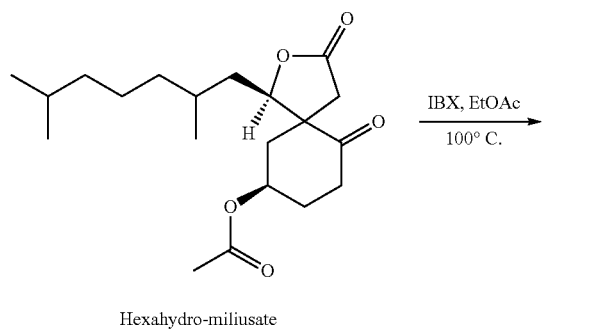

Hexahydro-miliusate

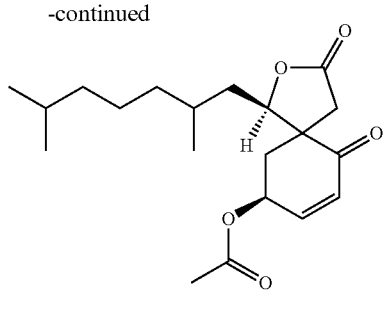

2′, 3′, 6′, 7′-Tetrahydro-miliusate

The new molecules 2′,3′,6′,7′-tetrahydro-miliusate is thus synthesized (see Scheme 6).

General Method for Preparation of 2-Hydroxy-Miliusane Derivatives. To a stirred solution of a miliusane such as miliusate (20 mg, 0.058 mmol) in MeOH (5 mL) is added sodium borohydride (NaBH₄) (2.2 mg, 1 eq) at 0° C. The reaction mixture is stirred at 0° C. for 1 hour, quenched with saturated ammonium chloride (NH₄Cl) (10 mL), and then extracted with EtOAc (3×20 mL). The combined EtOAc solution is washed sequentially with H₂O (10 mL) and brine (10 mL), dried with Na₂SO₄), and concentrated in vacuo. The reaction mixture is subjected to chromatography separation on a silica gel column, eluted with a solvent system such as petroleum ether: EtOAc 2:1 to afford 2-hydroxy-miliusane derivative. Unreacted, partially reacted or unwanted compounds as disclosed herein should be removed from the reaction product.

SCHEME 7

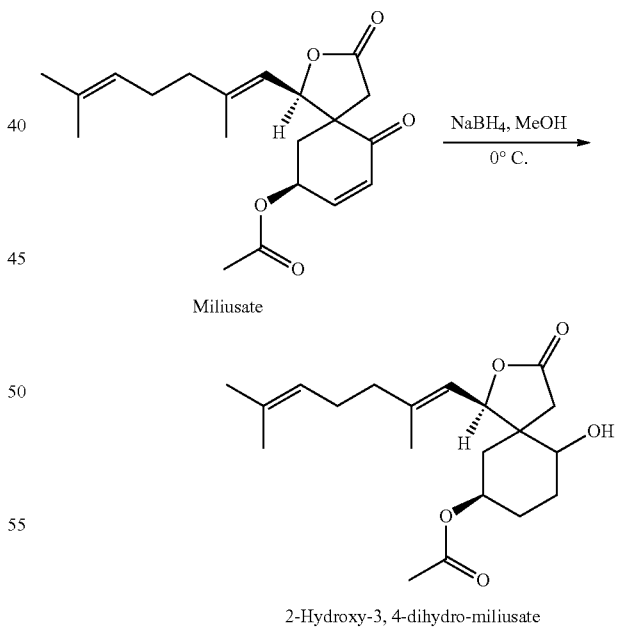

2-Hydroxy-3, 4-dihydro-miliusate

The new molecule 2-hydroxy-3,4-dihydro-miliusate is thus synthesized (see Scheme 7).

General Method for Preparation of Ester Derivatives of 2-Hydroxy-Miliusanes. A solution of a 2-hydroxy-miliusane such as 2-hydroxy-3,4-dihydro-miliusate (8 mg, 0.023 mmol) in CH₂Cl₂ (5 mL) is treated with triethylamine (TEA) (16.0 μL, 5 eq), anhydrous acetic acid (Ac₂O) (6.5 μL, 3 eq)

and catalytic amount of DMAP. The reaction mixture is stirred at room temperature for 3 hours, quenched with saturated NaHCO₃ (20 mL), and then extracted with EtOAc (3×10 mL). The combined EtOAc solution is washed with H₂O (10 mL) and brine (10 mL), dried with Na₂SO₄, and concentrated in vacuo. The mixture is chromatographed on a silica gel column, eluting with petroleum ether: EtOAc 4:1 to afford ester derivative of 2-hydroxy-miliusane. Unreacted, partially reacted or unwanted compounds as disclosed herein should be removed from the reaction product.

SCHEME 8

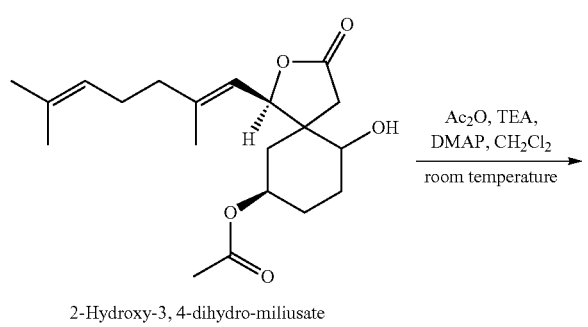

2-Hydroxy-3, 4-dihydro-miliusate

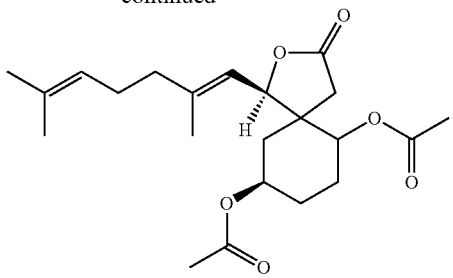

2-Acetoxy-3, 4-dihydro-miliusate

The new molecule 2-acetoxy-3,4-dihydro-miliusate is thus synthesized (see Scheme 8).

General Method for Preparation of Aldehyde and Hydroxy Derivatives on The Side Chain of Miliusanes. To a 25-mL flask is introduced 16 mg (0.5 eq) of selenium dioxide (SeO₂), 10 mL of CH₂Cl₂ and 80 μL (2 eq) of 70% tert-butyl hydroperoxide (TBHP). After the mixture is stirred for 0.5 hours at 25° C. (water bath), a miliusane such as miliusate (100 mg, 0.29 mmol) is added in several minutes. The mixture is stirred at 25° C. for 48 hours. The solvent is then removed in vacuo, and the residue is subjected to silica gel column chromatography separation to give side chain aldehyde and hydroxy derivatives of miliusanes. Unreacted, partially reacted or unwanted compounds as disclosed herein should be removed from the reaction product.

SCHEME 9

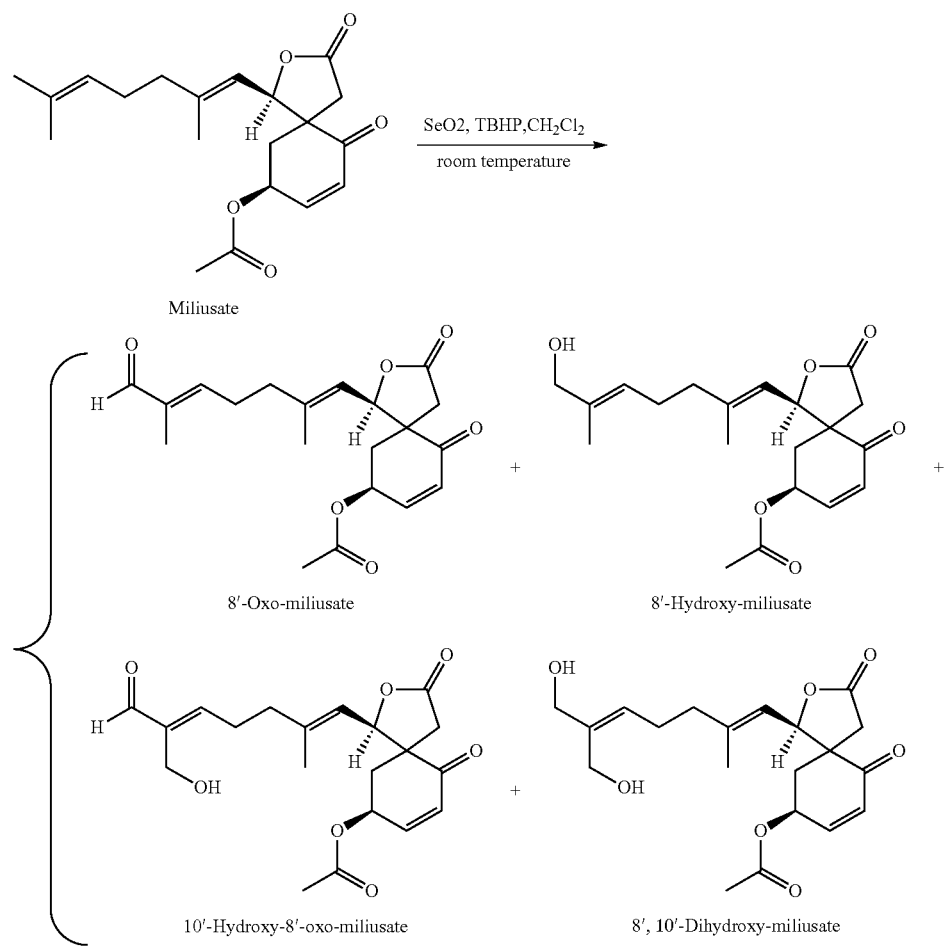

The new molecules 8'-oxo-miliusate, 8'-hydroxy-miliusate, 10'-hydroxy-8'-oxo-miliusate, and 8',10'-dihydroxy-miliusate are thus synthesized (see Scheme 9).

General Method for Preparation of Miliusol Ester Derivatives. The solution of 5.0 mg of miliusane such as miliusol (0.016 mmol) in 1.0 mL of dry pyridine is pipetted into a solution of selected acyl chloride reagent such as p-dimethyl-benzoyl chloride (0.2 mmol) in 1.0 mL of dry pyridine at 0° C. The reaction is allowed to proceed at 0° C. for 2 hours, and additional 20 hours at room temperature. The reaction product is evaporated in vacuo to dryness to afford a mixture, which is subjected to a Si gel column separation to afford acyl-miliusane ester. Unreacted, partially reacted or unwanted compounds as disclosed herein should be removed from the reaction product. The molecule 5β-(p-dimethylamino-benzoyl)miliusol is thus synthesized (see Scheme 10).

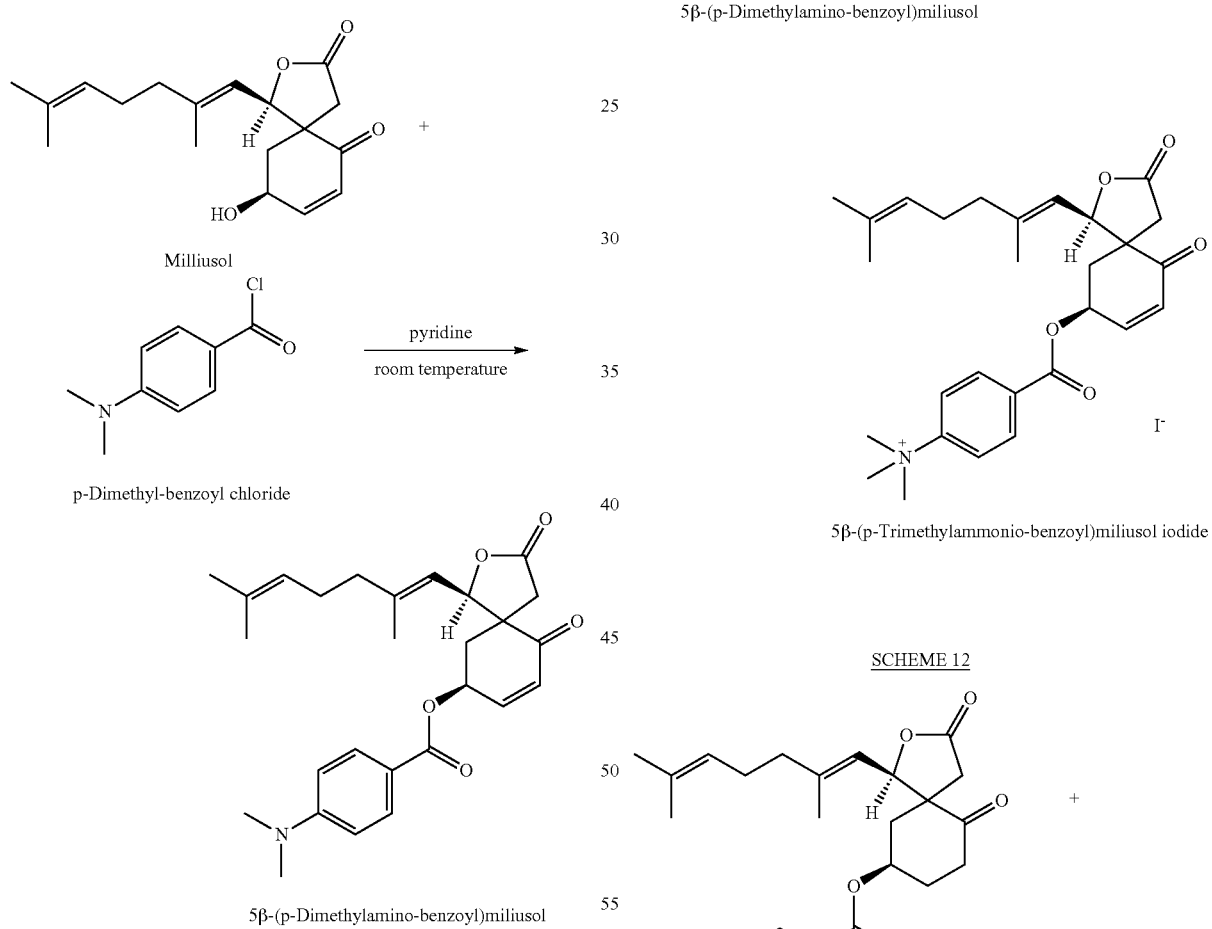

General Method for Preparation of Miliusane Ammonium Salts. A chloroform (CHCl$_3$) solution of an amino group containing miliusane derivative such as 5β-(p-dimethyl-amino-benzoyl)miliusol (10 mg, 0.022 mmol) of in an alkyl halide such as methyl iodide and allyl bromide (10 mL) is refluxed under N$_2$ atmosphere for 72 hours. Products can be detected by TLC, HPLC and LC-MS. The reaction product is evaporated in vacuo to dryness to afford a mixture, which is subjected to a Si gel column separation to afford miliusane ammonium salt product. Unreacted, partially reacted or unwanted compounds as disclosed herein should be removed from the reaction product.

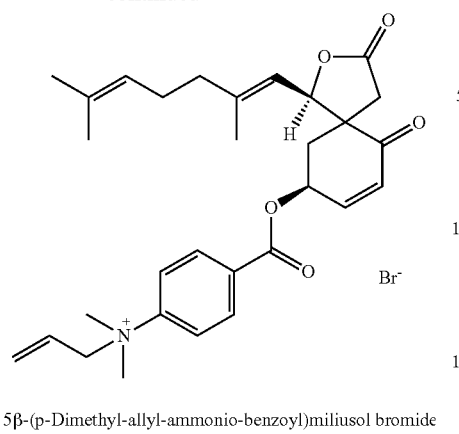

5β-(p-Dimethyl-allyl-ammonio-benzoyl)miliusol bromide

The new molecules 5β-(p-trimethylammonio-benzoyl) miliusol iodide and 5β-(p-dimethyl-allyl-ammonio-benzoyl) miliusol bromide are thus synthesized (see Schemes 11 and 12).

General Method for Preparation of Miliusane lactam. A mixture of a miliusane such as miliusol (6.1 mg, 0.02 mmol), a primary amine such as n-butylamine (5.9 μL, 0.06 mmol) and aniline (5.5 μL, 0.06 mmol) and 1-butyl-3-methylimidazolium tetrafluoroborate ([bmim]BF$_4$, 3.7 μL, 0.02 mmol) is vortexed in a sealed vessel for 30 seconds prior to microwave irradiation at 220° C. for 35 minutes. The cooled reaction mixture is then diluted with 5 mL of EtOAc and washed with saturated aqueous NH$_4$Cl. The collected EtOAc solution is concentrated in vacuo, and purified over a silica gel column to afford miliusane lactam product. Unreacted, partially reacted or unwanted compounds as disclosed herein should be removed from the reaction product.

SCHEME 13

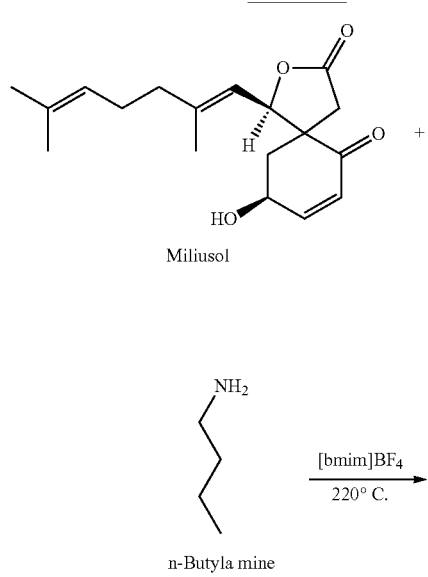

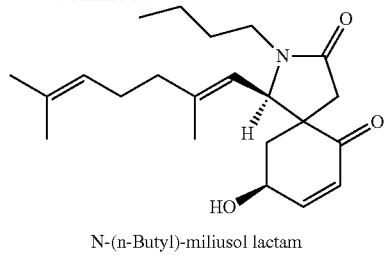

N-(n-Butyl)-miliusol lactam

SCHEME 14

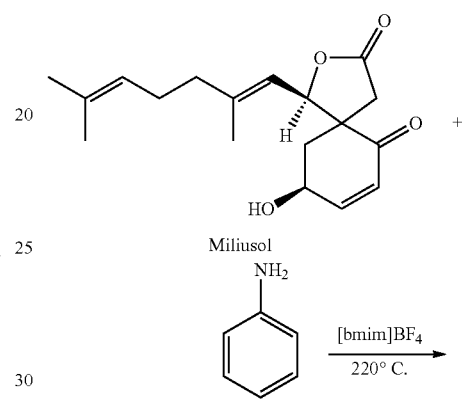

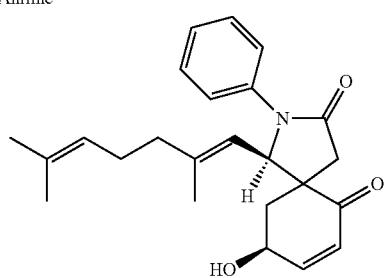

N-Phenyl-miliusol lactam

The new molecules N-(n-butyl)-miliusol lactam and N-phenyl-miliusol lactam are thus synthesized (see Schemes 13 and 14).

4β-(N-Phenyl)miliusate is obtained as a white powder with a molecular formula of C$_{26}$H$_{33}$NO$_5$ determined by positive HRESIMS and NMR studies. $^1$H NMR (400 MHz, CDCl$_3$, J in Hz) δ (in ppm with reference to the signal of CDCl$_3$ at δ 7.24 ppm) phenyl protons [7.18 (2H, brt, J=7.5), 6.79 (1H, brt, J=6.7), 6.60 (2H, brs)], 5.58 (1H, d, J=10.6, H-1'), 5.48 (1H, brs, H-5), 4.96 (1H, brd, J=10.8, H-2'), 4.94 (1H, m, H-6'), 3.81 (1H, brdt, J=13.1, 3.5, H-4), 3.57 (1H, d, J=18.1, H-7β), 2.76 (1H, brdd, J=13.1, 3.1, H-3α), 2.66 (1H, dd, J=15.7, 2.7, H-6β), 2.48 (1H, brt, J=13.1, H-3β), 2.24 [3H, s, OC(=O)CH$_3$], 2.00 (1H, d, J=18.0, H-7α), 2.02 (4H, m, H$_2$-4' and H$_2$-5'), 1.84 (3H, d, J=1.3 Hz, CH$_3$-9'), 1.75 (1H, dd, J=15.6, 3.3, H-6α), 1.63 (3H, s, CH$_3$-8'), 1.55 (3H, s, CH$_3$-10'). HRTOF positive ESIMS m/s calcd for C$_{26}$H$_{33}$NO$_5$: 440.2432 [M+1]$^+$, found: 440.2425 [M+1]$^+$.

4α-(N-Phenyl)miliusate is obtained as a white powder with a molecular formula of C$_{26}$H$_{33}$NO$_5$ determined by positive HRESIMS and NMR studies. $^1$H NMR (400 MHz, CDCl$_3$, J in Hz) δ (in ppm with reference to the signal of CDCl$_3$ at δ 7.24 ppm) phenyl protons [7.21 (2H, brt, J=7.8), 6.79 (3H, m)], 5.81 (1H, d, J=10.6, H-1'), 5.38 (1H, brq, J=2.9, H-5), 5.01 (1H, brd, J=10.7, H-2'), 4.95 (1H, m, H-6'), 4.04 (1H, m, H-4), 3.57 (1H, d, J=18.1, H-7β), 2.81 (1H, dd, J=14.0, 4.6, H-3β), 2.40 (1H, brd, J=15.3, H-6β), 2.39 (1H, brd, J=13.2, H-3α), 2.23 [3H, s, OC(=O)CH$_3$], 2.16 (1H, dd, J=15.4, 3.8, H-6α), 2.08 (1H, d, J=18.3, H-7α), 2.04 (4H, m, H$_2$-4' and H$_2$-5'), 1.86 (3H, d, J=1.3 Hz, CH$_3$-9'), 1.66 (3H, s, CH$_3$-8'), 1.57 (3H, s, CH$_3$-10'). HRTOF positive ESIMS m/s calcd for C$_{26}$H$_{33}$NO$_5$: 440.2432 [M+1]$^+$, found: 440.2436 [M+1]1$^+$.

4β-(N-Benzoyl-N-phenyl)miliusate is obtained as a white powder with a molecular formula of C$_{33}$H$_{37}$NO$_6$ determined by positive HRESIMS and NMR studies. $^1$H NMR (400 MHz, CDCl$_3$, J in Hz) δ (in ppm with reference to the signal of CDCl$_3$ at δ 7.24 ppm) aromatic protons [7.06-7.25 (8H, m), 6.93-7.00 (2H, m)], 5.66 (1H, brtd, J=8.3, 4.9, H-5), 5.22 (1H, brd, J=10.0, H-2'), 5.10 (1H, d, J=10.0, H-1'), 4.99 (1H, m, H-6'), 4.60 (1H, brtd, J=8.0, 5.9, H-4), 3.33 (1H, d, J=17.4, H-7β), 2.87 (1H, dd, J=16.6, 5.8, H-3α), 2.74 (1H, dd, J=16.6, 8.4, H-3β), 2.42 (1H, d, J=17.5, H-7α), 2.19 (1H, dd, J=13.9, 4.9, H-6β), 2.11 (1H, dd, J=14.0, 8.9, H-6α), 2.09 [3H, s, OC(=O)CH$_3$], 2.05 (4H, m, H$_2$-4' and H$_2$-5'), 1.76 (3H, d, J=1.3 Hz, CH$_3$-9'), 1.64 (3H, s, CH$_3$-8'), 1.57 (3H, s, CH$_3$-10'). HRTOF positive ESIMS m/s calcd for C$_{33}$H$_{37}$NO$_6$: 544.2694 [M+1]$^+$, found: 544.2690 [M+1]$^+$.

4α-(N-Benzoyl-N-phenyl)miliusate is obtained as a white powder with a molecular formula of C$_{33}$H$_{37}$NO$_6$ determined by positive HRESIMS and NMR studies. $^1$H NMR (400 MHz, CDCl$_3$, J in Hz) δ (in ppm with reference to the signal of CDCl$_3$ at δ 7.24 ppm) aromatic protons [7.06-7.22 (8H, m), 6.97-7.01 (2H, m)], 5.94 (1H, brq, J=2.2, H-5), 5.58 (1H, d, J=10.6, H-1'), 5.00 (1H, brddd, J=14.8, 3.9, 2.7, H-4), 4.92 (1H, brdd, J=10.6, 1.0, H-2'), 4.88 (1H, m, H-6'), 3.57 (1H, d, J=18.0, H-7β), 2.79 (1H, dd, J=14.9, 13.1, H-3β), 2.55 (1H, brdd, J=15.6, 2.9, H-6β), 2.48 (1H, brdd, J=13.0, 3.9, 1.2, H-3α), 2.05 [3H, s, OC(=O)CH$_3$], 1.96 (4H, m, H$_2$-4' and H$_2$-5'), 1.88 (1H, dd, J=15.6, 3.4, H-6α), 1.98 (1H, d, J=18.2, H-7α), 1.67 (3H, d, J=1.3 Hz, CH$_3$-9'), 1.62 (3H, s, CH$_3$-8'), 1.52 (3H, s, CH$_3$-10'). HRTOF positive ESIMS m/s calcd for C$_{33}$H$_{37}$NO$_6$: 544.2694 [M+1]$^+$, found: 544.2699 [M+1]$^+$.

Hexadehydro-miliusate is obtained as a white powder with a molecular formula of C$_{20}$H$_{32}$O$_5$ determined by positive HRESIMS and NMR studies. $^1$H NMR (400 MHz, CDCl$_3$, J in Hz) δ (in ppm with reference to the signal of CDCl$_3$ at δ 7.24 ppm) 5.29 (1H, brquintet, J=3.2, H-5), 5.01 (1H, brdd, J=11.6, 2.1, H-1'), 3.43 (1H, d, J=17.9, H-7β), 2.41-2.64 (3H, m), 2.28 (1H, m), 2.13 [3H, s, OC(=O)CH$_3$], 2.04 (1H, m), 2.01 (1H, d, J=17.9, H-7α), 1.83 (1H, dd, J=15.2, 3.7, H-6α), 1.68 (1H, m), 1.27-1.56 (4H, m), 0.94-1.28 (5H, m), 0.88 (3H, d, J=6.7 Hz), 0.84 (3H, d, J=6.6 Hz), 0.83 (3H, d, J=6.6 Hz). HRTOF positive ESIMS m/s calcd for C$_{20}$H$_{32}$O$_5$: 353.2323 [M+1]$^+$, found: 353.2318 [M+1]$^+$.

3,4-Didehydro-miliusate is obtained as a white powder with a molecular formula of C$_{20}$H$_{28}$O$_5$ determined by positive HRESIMS and NMR studies. $^1$H NMR (400 MHz, CDCl$_3$, J in Hz) δ (in ppm with reference to the signal of CDCl$_3$ at δ 7.24 ppm) 5.74 (1H, d, J=10.6, H-1'), 5.27 (1H, brquintet, J=3.0, H-5), 4.98 (1H, brdd, J=10.6, 1.0, H-2'), 4.94 (1H, m, H-6'), 3.54 (1H, d, J=18.0, H-7β), 2.55 (1H, brdt, J=15.3, 3.0), 2.42 (1H, brtd, J=14.6, 6.1), 2.30 (1H, brdd, J=13.4, 5.8, 2.9), 2.25 (1H, m), 2.15 [3H, s, OC(=O)CH$_3$], 2.01 (4H, m, H$_2$-4' and H$_2$-5'), 2.00 (1H, d, J=18.0, H-7α), 1.96 (2H, m), 1.82 (3H, d, J=1.3 Hz, CH$_3$-9'), 1.64 (3H, s, CH$_3$-8'), 1.55 (3H, s, CH$_3$-10'). HRTOF positive ESIMS m/s calcd for C$_{20}$H$_{28}$O$_5$: 349.2010 [M+1]+, found: 349.2005 [M+1]$^+$.

2',3',6',7'-Tetradehydro-miliusate is obtained as a white powder with a molecular formula of C$_{26}$H$_{33}$NO$_5$ determined by positive HRESIMS and NMR studies. $^1$H NMR (400 MHz, CDCl$_3$, J in Hz) δ (in ppm with reference to the signal of CDCl$_3$ at δ 7.24 ppm) 6.87 (1H, brddd, J=10.2, 4.2, 1.8, H-4), 6.16 (1H, brdd, J=10.2, 1.1, H-3), 5.52 (1H, brqd, J=4.0, 1.1, H-5), 4.72 (1H, brdd, J=10.8, 2.6, H-1'), 3.20 (1H, d, J=17.5, H-7β), 2.37 (1H, brdtd, J=14.9, 3.9, 0.9), 2.26 (1H, brdt, J=14.7, 4.2), 2.25 (1H, d, J=17.6, H-7α), 2.11 [3H, s, OC(=O)CH$_3$], 1.83 (1H, dd, J=15.2, 3.7, H-6α), 1.40-1.60 (2H, m), 0.93-1.40 (7H, m), 0.88 (3H, d, J=6.7 Hz), 0.83 (6H, d, J=6.5 Hz). HRTOF positive ESIMS m/s calcd for C$_{20}$H$_{30}$O$_5$: 351.2166 [M+1]$^+$, found: 351.2156 [M+1]+.

2-Hydroxy-3,4-didehydro-miliusate is obtained as a white powder with a molecular formula of C$_{20}$H$_{30}$O$_5$ determined by positive HRESIMS and NMR studies. $^1$H NMR (400 MHz, CDCl$_3$, J in Hz) δ (in ppm with reference to the signal of CDCl$_3$ at δ 7.24 ppm) 5.24 (1H, brd, J=10.4, H-2'), 4.99 (1H, m, H-6'), 4.82 (1H, d, J=10.5, H-1'), 4.76 (1H, brseptet, J=4.7, H-5), 3.70 (1H, brs, H-2), 2.47 (1H, d, J=17.3, H-7β), 2.33 (1H, brdd, J=17.3, 1.4, H-7α), 2.07-2.24 (5H, m), 2.02 [3H, s, OC(=O)CH$_3$], 1.98 (1H, brt, J=11.4), 1.77-1.92 (4H, m), 1.74 (3H, d, J=1.3 Hz, CH$_3$-9'), 1.67 (3H, s, CH$_3$-8'), 1.60 (3H, s, CH$_3$-10'). HRTOF positive ESIMS m/s calcd for C$_{20}$H$_{30}$O$_5$: 351.2166 [M+1]$^+$, found: 351.2160 [M+1]$^+$.

2-Acetoxy-3,4-didehydro-miliusate is obtained as a white powder with a molecular formula of C$_{22}$H$_{32}$O$_6$ determined by positive HRESIMS. HRTOF positive ESIMS m/s calcd for C$_{22}$H$_{32}$O$_6$: 393.2272 [M+1]$^+$, found: 393.2266 [M+1]$^+$.

8'-Oxo-miliusate is obtained as a white powder with a molecular formula of C$_{20}$H$_{24}$O$_6$ determined by positive HRESIMS and NMR studies $^1$H NMR (400 MHz, CDCl$_3$, J in Hz) δ (in ppm with reference to the signal of CDCl$_3$ at δ 7.24 ppm) 9.37 (1H, s, H-8'), 6.81 (1H, brddd, J=10.2, 4.0, 0.8, H-4), 6.33 (1H, brtq, J=7.1, 1.3, H-6'), 6.00 (1H, brdd, J=10.2, 1.2, H-3), 5.55 (1H, brq, J=4.2, H-5), 5.45 (1H, d, J=9.9, H-1'), 5.19 (1H, brdq, J=9.9, 1.3, H-2'), 3.31 (1H, d, J=17.6, H-7β), 2.43 (1H, brt, J=7.5, H-5'a), 2.41 (1H, brt, J=7.3, H-5'b), 2.36 (1H, brddd, J=14.6, 4.3, 0.9, H-6β), 2.27 (1H, d, J=17.6, H-7α), 2.24 (1H, dd, J=14.7, 5.5, H-6α), 2.19 (2H, brt, J=7.3, H$_2$-4'), 2.13 [3H, s, OC(=O)CH$_3$], 1.70 (3H, brd, J=1.1 Hz, CH$_3$-10'), 1.69 (3H, d, J=1.3 Hz, CH$_3$-9'). HRTOF positive ESIMS m/s calcd for C$_{20}$H$_{24}$O$_6$: 361.1646 [M+1]+, found: 361.1640 [M+1]+.

8'-Hydroxy-miliusate is obtained as a white powder with a molecular formula of C$_{20}$H$_{26}$O$_6$ determined by positive HRESIMS and NMR studies $^1$H NMR (400 MHz, CDCl$_3$, J in Hz) δ (in ppm with reference to the signal of CDCl$_3$ at δ 7.24 ppm) 6.83 (1H, brddd, J=10.3, 4.3, 1.3, H-4), 6.08 (1H, brdd, J=10.2, 1.2, H-3), 5.57 (1H, d, J=10.1, H-1'), 5.56 (1H, m, H-5), 5.17 (1H, m, H-6'), 5.05 (1H, brdq, J=10.1, 1.0, H-2'), 4.01 (1H, ABbrd, J=13.5, H-8'a), 3.95 (1H, ABbrd, J=13.4, H-8'b), 3.43 (1H, d, J=17.7, H-7β), 2.44 (1H, brddd, J=15.0, 3.2, 1.4, H-6β), 2.23 (1H, dd, J=15.1, 5.5, H-6α), 2.18 (1H, d, J=17.7, H-7α), 2.14 [3H, s, OC(=O)CH$_3$], 2.12 (2H, m, H$_2$-5'), 2.07 (2H, m, H$_2$-4'), 1.65 (3H, d, J=1.3 Hz, CH$_3$-9'), 1.61 (3H, s, CH$_3$-10'). HRTOF positive ESIMS m/s calcd for C$_{20}$H$_{26}$O$_6$: 363.1802 [M+1]$^+$, found: 363.1808 [M+1]$^+$.

10'-Hydroxy-8'-oxo-miliusate is obtained as a white powder with a molecular formula of C$_{20}$H$_{24}$O$_7$ determined by positive HRESIMS and NMR studies. $^1$H NMR (400 MHz, CDCl$_3$, J in Hz) δ (in ppm with reference to the signal of CDCl$_3$ at δ 7.24 ppm) 9.42 (1H, s, H-8'), 6.82 (1H, brddd, J=10.2, 3.9, 0.8, H-4), 6.45 (1H, brt, J=7.4, H-6'), 6.02 (1H, brdd, J=10.2, 1.2, H-3), 5.56 (1H, brq, J=4.2, H-5), 5.45 (1H, d, J=9.9, H-1'), 5.21 (1H, brdq, J=9.9, 1.2, H-2'), 4.35 (1H, ABd, J=12.8, H-10'a), 4.30 (1H, ABd, J=12.7, H-10'b), 3.32 (1H, d, J=17.6, H-7β), 2.53 (1H, brtd, J=7.6, 2.3, H-5'a), 2.51 (1H, brt, J=7.4, H-5'b), 2.39 (1H, brddd, J=14.6, 4.3, 0.7, H-6β), 2.26 (1H, d, J=17.7, H-7α), 2.23 (2H, brt J=7.1, H$_2$-4'), 2.23 (1H, overlap, H-6α), 2.14 [3H, s, OC(=O)CH$_3$], 1.70 (3H, d, J=1.3 Hz, CH$_3$-9'). HRTOF positive ESIMS m/s calcd for C$_{20}$H$_{24}$O$_7$: 377.1595 [M+1]$^+$, found: 377.1600 [M+1]$^+$.

8',10'-Dihydroxy-miliusate is obtained as a white powder with a molecular formula of C$_{20}$H$_{26}$O$_7$ determined by positive HRESIMS and NMR studies. $^1$H NMR (400 MHz, CDCl$_3$, J in Hz) δ (in ppm with reference to the signal of CDCl$_3$ at δ 7.24 ppm) 9.42 (1H, s, H-8'), 6.83 (1H, brddd, J=10.2, 4.1, 1.1, H-4), 6.10 (1H, brdd, J=10.2, 1.1, H-3), 5.56 (1H, brq, J=4.1, H-5), 5.50 (1H, d, J=10.0, H-1'), 5.31 (1H, brt, J=7.1, H-6'), 5.08 (1H, brdq, J=10.0, 1.2, H-2'), 4.25 (1H, ABd, J=12.8, H-10'a), 4.21 (1H, ABd, J=12.8, H-10'b), 4.19 (1H, ABd, J=13.0, H-8'a), 4.15 (1H, ABd, J=13.0, H-8'b), 3.36 (1H, d, J=17.7, H-7β), 1.63 (2H, brs, 2×OH), 2.40 (1H, brddd, J=14.9, 3.7, 1.1, H-6β), 2.23 (1H, dd, J=14.9, 5.5, H-6α), 2.22 (1H, d, J=17.9, H-7α), 2.17 (1H, brt, J=6.7, H-5'a), 2.16 (1H, brt, J=7.2, H-5'b), 2.13 [3H, s, OC(=O)CH$_3$], 2.07 (2H, brt J=6.7, H$_2$-4'), 1.65 (3H, d, J=1.3 Hz, CH$_3$-9'). HRTOF positive ESIMS m/s calcd for C$_{20}$H$_{26}$O$_7$: 379.1751 [M+1]+, found: 379.1750 [M+1]+.

5β-(p-Trimethylammonio-benzoyl)miliusol iodide is obtained as a white powder with a molecular formula of C$_{28}$H$_{36}$NO$_5$I determined by positive HRESIMS. HRTOF positive ESIMS m/s calcd for C$_{28}$H$_{36}$NO$_5$: 466.2588 [M]$^+$, found: 466.2579 [M]$^+$.

5β-(p-Dimethyl-allyl-ammonio-benzoyl)miliusol bromide is obtained as a white powder with a molecular formula of C$_{30}$H$_{38}$NO$_5$Br determined by positive HRESIMS. HRTOF positive ESIMS m/s calcd for C$_{30}$H$_{38}$NO$_5$: 492.2745 [M]$^+$, found: 492.2735 [M]$^+$.

N-(n-Butyl)-miliusol lactam is obtained as a white powder with a molecular formula of C$_{22}$H$_{33}$NO$_3$ determined by positive HRESIMS. HRTOF positive ESIMS m/s calcd for C$_{22}$H$_{34}$NO$_3$: 360.2539 [M+1]$^+$, found: 360.2530 [M+1]$^+$.

N-Phenyl-miliusol lactam is obtained as a white powder with a molecular formula of C$_{24}$H$_{29}$NO$_3$ determined by positive HRESIMS. HRTOF positive ESIMS m/s calcd for C$_{24}$H$_{34}$NO$_3$: 380.2226 [M+1]+, found: 380.2235 [M+1]+.

Cell Culture Panel Bioassays. All pure compounds of the present invention are evaluated against human cancer cell lines using a cytotoxicity screening panel. Cytotoxicity assays involving oral epidermoid (KB), colon (HCT116), prostate (LNCaP), breast (MCF-7), lung (A549) and melanoma (A375) carcinoma cell lines, are performed using sulforhodamine B according to established protocols (Zhang H J, Ma C Y, Hung N V, Cuong N M, Tan G T, Santarsiero B D, Mesecar A D, Soejarto D D, Pezzuto J M, Fong H H S. Miliusanes, a class of cytotoxic agents from *Miliusa sinensis*. Journal of Medicinal Chemistry 2006; 49: 693-708; and Jutiviboonsuk A, Zhang H J, Tan G T, Ma C M, Hung N V, Cuong N M, Bunyapraphatsara N, Soejarto D D, Fong H H S. Bioactive constituents from the roots of *Bursera tonkinensis*. Phytochemistry 2005; 66: 2745-2751.). KB cells are maintained in DMEM medium. LNCaP cells are maintained in RPMI1640 medium with hormone-free 10% heat-activated FBS (fetal bovine serum) supplemented with 0.1 nM testosterone. MCF-7 cells are maintained and assayed in MEME medium containing 10 mg/L of insulin. HCT116 cells are maintained in McCoy's 5A medium supplemented with 10% fetal bovine serum. A549 and A375 cells are maintained in RPMI-1640 medium supplemented with 10% FCS. Serial dilutions of the compounds are prepared using 10% aqueous DMSO as solvent. The 190 μL cell suspension (3×10$^4$ cells in 1 ml media) is incubated with 10 μL sample solutions, in triplicate, in 96-well tissue culture plate at 37° C. in a humidified atmosphere of 5% CO$_2$ in air for 72 hours. 10 μL 10% aqueous DMSO is used as control group. Then the cells are fixed to plastic substratum by the addition of 100 μL cold 20% aqueous trichloroacetic acid and washing with water after incubation at 4° C. for 30 min. After staining cells with 100 μL of 0.4% sulforhodamine B in 1% aqueous AcOH for 30 min, unbound dye is removed by rinsing with 1% aqueous AcOH. The bound dye is solubilized with 200 μL 10 mM unbuffered Tris base, pH 10, and the optical density is measured at 515 nm using an ELISA plate reader. The average data are expressed as a percentage, relative to the control. The IC$_{50}$ values, the dose that inhibit cell growth by 50%, are calculated using nonlinear regression analysis (percent survival versus concentration).

Antitumor animal study. 4β-(N-Phenyl)miliusate shows potent cell killing activity in our in vitro evaluation system. In order to determine its antitumor activity, HCT116 xenograft animal study is used to evaluate the anticancer activity of 4β-(N-phenyl)miliusate in comparison with the clinically used anticancer drug paclitaxel. All animal studies are approved and performed according to Animal Care and Use Guidelines of the Animal Ethics Committee at Hong Kong Baptist University and performed following Animal Care and Use guidelines set by NIH (National Institute of Health, USA). BALB/c nude mice, SPF class, male or female, 7-8 weeks old, are purchased from Charles River Laboratories. Before the experiment, the mice are kept for one week of acclimatization to SPF class laboratory conditions. 4β-(N-Phenyl)miliusate was tested for its antitumor activity against HCT116 cancer cells using a number of nude mice (Balc/nu/nu, female) in comparison of paclitaxel. HCT116 cancer cells are subcutaneously implanted with 5×10$^6$ cells in the rear flank of each mouse. After 10 days, solid tumors with average size of about 80 mm$^3$ appeared at the implanted sites. The mice are then divided into three groups: one dose (20 mg/kg: 10 mice) group of 4β-(N-phenyl)miliusate, one dose (10 mg/kg: 10 mice) of paclitaxel and one dose of vechicle (negative control: 10 mice). Every other day injections at i.p. sites are scheduled for 21 days. Weights of mice and tumor diameters are measured twice a week until the end of the experiment. The tumor size in mm$^3$ is calculated by the formula: tumor size=length×width×height (L×W×H).

Having now fully described the present invention in some detail by way of illustration and examples for purposes of clarity of understanding, it will be obvious to one of ordinary skill in the art that the same can be performed by modifying or changing the present invention within a wide and equivalent range of conditions, formulations and other parameters without affecting the scope of the present invention or any specific embodiment thereof, and that such modifications or changes are intended to be encompassed within the scope of the appended claims. The terms and expressions which have been employed are used as terms of description and not of limitation, and there is no intention that in the use of such terms and expressions of excluding any equivalents of the features shown and described or portions thereof, but it is recognized that various modifications are possible within the scope of the present invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of the present invention.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the present invention, unless otherwise stated. Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, additional cells, and additional uses of the present invention. All headings used herein are for convenience only. All patents and publications mentioned in the specification are indicative of the levels of skill of those skilled in the art to which the present invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extent. All publications recited herein are hereby incorporated by reference in their entirety.

INDUSTRIAL APPLICABILITY

The present invention discloses new anticancer agents based on the miliusane natural products. The present invention also includes its preparation and application method for treating cancer.

What is claimed is:
1. A compound comprising formula (I):

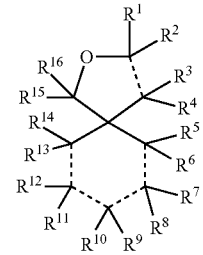

wherein
$R^1$ and $R^2$ are independently substituted by hydrogen, or taken together with the carbon atoms to which they are attached to form a carboxyl group (C=O);
$R^3$ and $R^4$ are independently substituted by hydrogen, halogen, hydroxy, hydrocarbyl or taken together with the carbon atoms to which they are attached to form a carboxyl group (C=O);
$R^5$ and $R^6$ are each independently substituted by halogen, $R^{19}$, —$OR^{19}$ or taken together with the carbon atoms to which they are attached to form a carboxyl group (C=O);
at least one of the carbons to which $R^7$, $R^8$, $R^9$, $R^{10}$, $R^{11}$ and $R^{12}$ are attached is not oxygenated carbon (C—O and C=O);
while one substituent of $R^7$ and $R^8$, one substituent of $R^9$ and $R^{10}$, or one substituent of $R^{11}$ and $R^{12}$ is hydrogen, —$OR^{19}$ or halogen whereas the other substituent of $R^7$ and $R^8$, the other substituent of $R^9$ and $R^{10}$, or the other substituent of $R^{11}$ and $R^{12}$ is selected from hydrogen, —$OR^{19}$, halogen, $N(R^{17})R^{18}$ or —$N(R^{17})C(=O)R^{18}$;
$R^{13}$ and $R^{14}$ are independently substituted by hydrogen, hydroxy, or taken together with the carbon atoms to which they are attached to form a carboxyl group (C=O);
$R^{15}$ and $R^{16}$ are independently substituted by hydrogen, or hydrocarbyl, wherein said hydrocarbyl has at least five carbons, and may be optionally substituted with one, two, or three substituents independently selected from hydroxy, halogen, aldehyde group (H—C=O), $C_{1-6}$ alkyl or $C_{1-6}$ alkoxy;
$R^{17}$ and $R^{18}$ are independently selected from hydrogen, hydrocarbyl optionally substituted with one, two, three, four or five of $R^{20}$, heterocyclyl optionally substituted with one, two, three, four or five of $R^{20}$ and —(CH$_2$)

$_k$-heterocyclyl optionally substituted with one, two, three, four or five of $R^{20}$; wherein k is an integer between 1 and 6;

$R^{19}$ is selected from $R^{21}$ and —C(=O)$R^{21}$, and $R^{19}$ is not selected from N-methyl-2-pyrrolecarboxyl and p-dimethylamino-benzoyl;

$R^{20}$ is independently selected from halogen, —O$R^{22}$, —C(=O)$R^{23}$, —C(=O)N($R^{22}$)$R^{23}$, —C(=O)O$R^{22}$, —OC(=O)$R^{23}$, —N($R^{22}$)$R^{23}$ and —N($R^{22}$)C(=O)$R^{23}$;

$R^{21}$ is selected from hydrogen, heterocyclyl optionally substituted with one, two, three, four or five of $R^{24}$, hydrocarbyl optionally substituted with one, two, three, four or five of $R^{24}$, and —(CH$_2$)$_k$-heterocyclyl optionally substituted with one, two, three, four or five of $R^{24}$; wherein k is an integer between 1 and 6;

$R^{22}$ and $R^{23}$ are each independently selected from hydrogen, or hydrocarbyl and —(CH$_2$)$_k$-heterocyclyl, either of which is optionally substituted with one, two, three, four or five substituents independently selected from halogen, cyano, amino, hydroxy, $C_{1-6}$ alkyl or $C_{1-6}$ alkoxy; wherein k is an integer between 1 and 6;

$R^{24}$ is selected from —N($R^{25}$)($R^{26}$) and —N($R^{25}$)($R^{26}$)$R^{27}$;

$R^{25}$, $R^{26}$ and $R^{27}$ are independently selected from hydrogen or hydrocarbyl;

dashed line denotes a single or double bond;

and a pharmaceutically acceptable salt or prodrug thereof.

2. The compound of claim 1, wherein said compound is an optically pure stereoisomer.

3. The compound of claim 1, wherein said compound is an enantiomer.

4. The compound of claim 1, wherein said compound is a racemate.

5. The compound of claim 1, wherein said compound is a diastereomer.

6. The compound of claim 1, wherein said compound is a tautomer.

7. A pharmaceutical composition comprising an effective amount of the compound of claim 1 and a pharmaceutically acceptable carrier thereof.

8. The compound of claims 1 is selected from 4β-(N-phenyl)miliusate, 4α-(N-phenyl)miliusate, 4β-(N-benzoyl-N-phenyl)miliusate, 4α-(N-benzoyl-N-phenyl)miliusate, hexahydro-miliusate, 3,4-dihydro-miliusate, 2',3',6',7'-tetrahydro-miliusate, 2-hydroxy-3,4-dihydro-miliusate, 2-acetoxy-3,4-dihydro-miliusate, 8'-oxo-miliusate, 8'-hydroxy-miliusate, 10'-hydroxy-8'-oxo-miliusate, 8',10'-dihydroxy-miliusate, 5β-(p-trimethylammonio-benzoyl)miliusol iodide, and 5β-(p-dimethyl-allyl-ammonio-benzoyl)miliusol bromide with the following formulae:

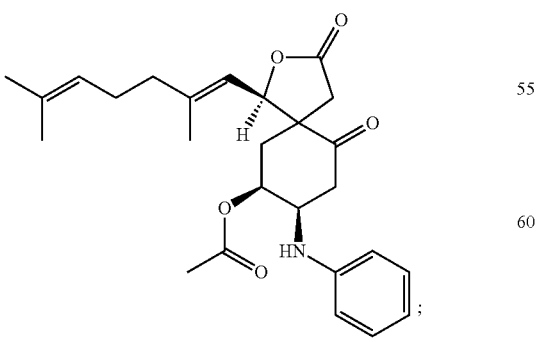

4β-(N-Phenyl)miliusate

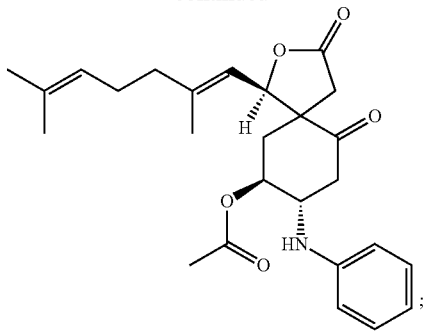

4α-(N-Phenyl)miliusate

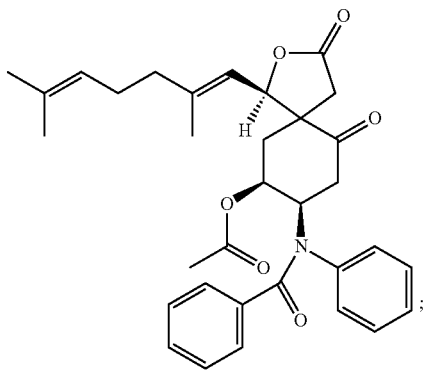

4β-(N-Benzoyl-N-phenyl)miliusate

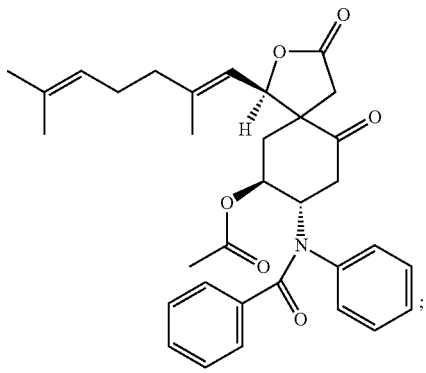

4α-(N-Benzoyl-N-phenyl)miliusate

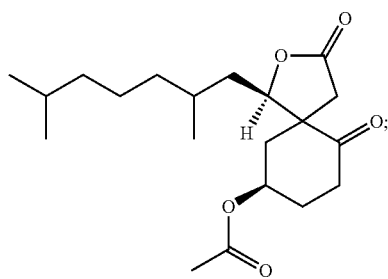

Hexahydro-miliusate

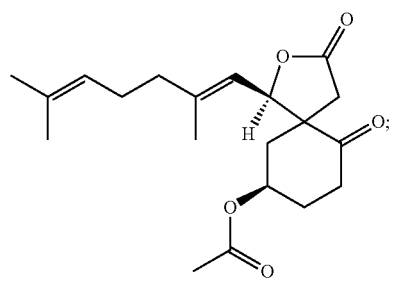
3,4-Dihydro-miliusate
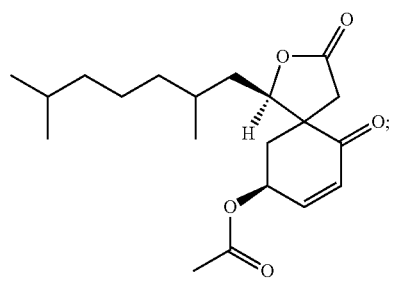
2′,3′,6′,7′-Tetrahydro-miliusate
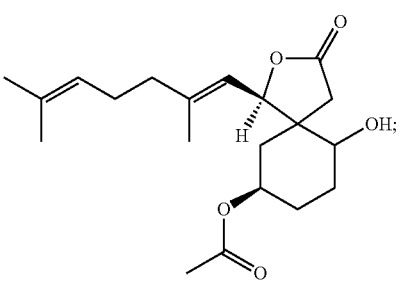
2-Hydroxy-3,4-dihydro-miliusate
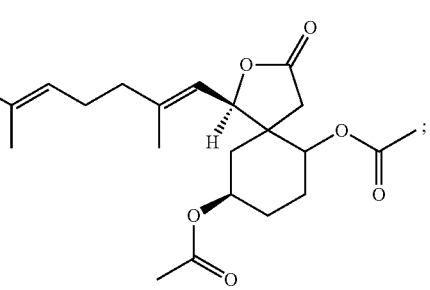
2-Acetoxy-3,4-dihydro-miliusate
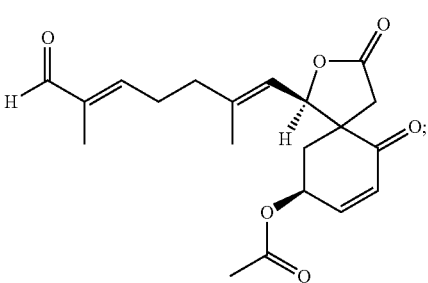
8′-Oxo-miliusate
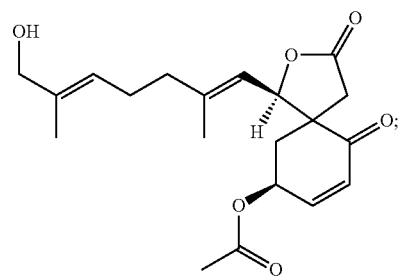
8′-Hydroxy-miliusate
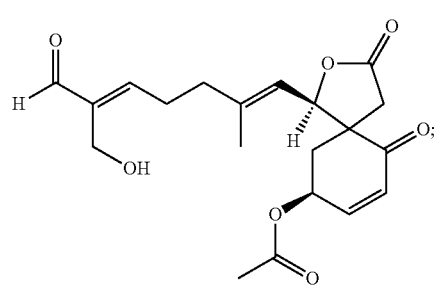
10′-Hydroxy-8′-oxo-miliusate
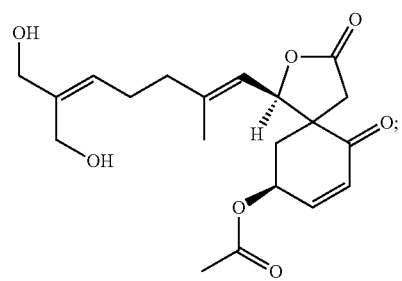
8′,10′-Dihydroxy-miliusate
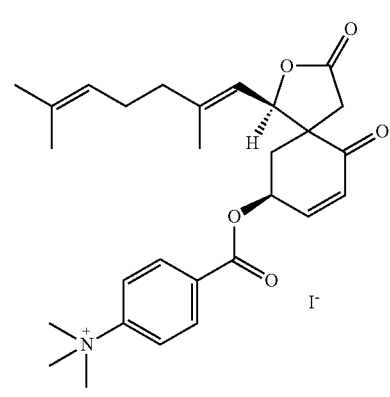
5β-(p-Trimethylammonio-benzyol)miliusol iodide;

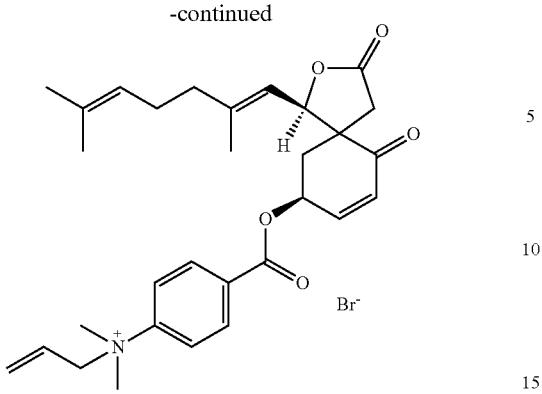
5β-(p-Dimethyl-allyl-ammonio-benzyol)miliusol bromide;
or a pharmaceutically acceptable salt or prodrug thereof.
* * * * *